US009265899B2

(12) United States Patent
Albrecht et al.

(10) Patent No.: US 9,265,899 B2
(45) Date of Patent: Feb. 23, 2016

(54) INSUFFLATING ACCESS SYSTEM

(75) Inventors: Jeremy J. Albrecht, Ladera Ranch, CA (US); Gary M. Johnson, Mission Viejo, CA (US); John R. Brustad, Dana Point, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 284 days.

(21) Appl. No.: 12/359,964

(22) Filed: Jan. 26, 2009

(65) Prior Publication Data
US 2009/0192444 A1 Jul. 30, 2009

Related U.S. Application Data

(60) Provisional application No. 61/023,539, filed on Jan. 25, 2008.

(51) Int. Cl.
A61M 13/00 (2006.01)
A61B 17/34 (2006.01)
A61B 17/00 (2006.01)

(52) U.S. Cl.
CPC .......... *A61M 13/003* (2013.01); *A61B 17/3474* (2013.01); *A61B 17/3439* (2013.01); *A61B 2017/00907* (2013.01); *A61B 2017/347* (2013.01); *A61B 2017/3441* (2013.01); *A61B 2017/3456* (2013.01)

(58) Field of Classification Search
CPC ........... A61B 17/3439; A61B 17/3474; A61B 2017/00907; A61B 2017/3441; A61B 2017/3456; A61B 2017/347; A61M 13/003

USPC ............................ 604/23, 26, 27, 96.01, 174, 604/164.01–164.09, 264, 158, 108, 43–47
See application file for complete search history.

(56) References Cited

U.S. PATENT DOCUMENTS

RE682 E 4/1859 Peale
184,573 A 11/1876 Becker
(Continued)

FOREIGN PATENT DOCUMENTS

BE 1 006 811 12/1994
CA 2 170 841 9/1997
(Continued)

OTHER PUBLICATIONS

The International Searching Authority/US, The International Search Report and Written Opinion for International Application No. PCT/US09/32026, entitled Insufflating Access System, mailed Mar. 23, 2009.
(Continued)

*Primary Examiner* — Kami A Bosworth
*Assistant Examiner* — Brandy S Lee
(74) *Attorney, Agent, or Firm* — Rimas T. Lukas

(57) ABSTRACT

Systems, devices, and methods permit insufflation of a body cavity prior to the insertion of a cannula into the body cavity. Some embodiments of an access system comprise an obturator, a trocar, and a fluid flow channel. The access system has a closed configuration, in which a distal end of the access system is fluidly isolated from the fluid flow channel, and an open configuration, in which the distal end of the access system is fluidly connected to the fluid flow channel, thereby permitting fluid flow, for example, an insufflation gas into a body cavity.

20 Claims, 19 Drawing Sheets

(56) References Cited

U.S. PATENT DOCUMENTS

| | | | |
|---|---|---|---|
| 207,932 A | 9/1878 | Alvord | |
| 224,513 A | 2/1880 | Burdon | |
| 396,754 A | 1/1889 | Mayfield | |
| 764,322 A | 7/1904 | Wiegand | |
| 1,147,408 A | 7/1915 | Kelis | |
| 1,672,258 A | 6/1928 | Hippenmeyer | |
| 1,727,495 A | 9/1929 | Wappler | |
| 1,845,727 A | 2/1932 | Slaughter | |
| 2,102,274 A | 12/1937 | Larimore | |
| 2,189,343 A | 2/1940 | Fritz | |
| 2,301,338 A | 11/1942 | Smith | |
| 2,434,594 A | 1/1948 | Schultz | |
| 2,441,143 A | 5/1948 | Gracey | |
| 2,646,701 A | 7/1953 | Lietin | |
| 2,699,770 A | 1/1955 | Fourestier et al. | |
| 2,764,148 A | 9/1956 | Sheldon | |
| 2,764,149 A | 9/1956 | Sheldon | |
| 2,769,355 A | 11/1956 | Henry | |
| 2,877,368 A | 3/1959 | Sheldon | |
| 2,932,294 A | 4/1960 | Fourestier et al. | |
| 3,005,468 A | 10/1961 | Erwin et al. | |
| 3,021,834 A | 2/1962 | Sheldon | |
| 3,033,226 A | 5/1962 | Allen | |
| 3,042,022 A | 7/1962 | Sheldon | |
| 3,224,320 A | 12/1965 | Knudsen | |
| 3,277,922 A | 10/1966 | Eisel | |
| 3,279,460 A | 10/1966 | Sheldon | |
| 3,357,433 A | 12/1967 | Fourestier et al. | |
| 3,385,553 A | 5/1968 | Braun | |
| 3,417,745 A | 12/1968 | Sheldon | |
| 3,437,747 A | 4/1969 | Sheldon | |
| 3,459,189 A | 8/1969 | Alley et al. | |
| 3,556,085 A | 1/1971 | Takahashi | |
| 3,613,684 A | 10/1971 | Sheridan | |
| 3,653,338 A | 4/1972 | Sauey | |
| 3,791,379 A | 2/1974 | Storz | |
| 3,817,251 A | 6/1974 | Hasson | |
| 3,821,956 A | 7/1974 | Gordhamer | |
| 3,870,036 A | 3/1975 | Fiore | |
| 3,961,621 A | 6/1976 | Northeved | |
| 3,971,385 A | 7/1976 | Corbett | |
| 3,994,287 A | 11/1976 | Turp | |
| 3,994,301 A | 11/1976 | Agris | |
| 4,028,987 A | 6/1977 | Wilson | |
| 4,112,932 A | 9/1978 | Chiulli | |
| 4,126,291 A | 11/1978 | Gilbert et al. | |
| 4,150,929 A | 4/1979 | Brandt | |
| 4,168,882 A | 9/1979 | Hopkins | |
| 4,180,068 A | 12/1979 | Jacobsen et al. | |
| 4,191,191 A | 3/1980 | Auburn | |
| 4,222,375 A | 9/1980 | Martinez | |
| 4,248,214 A | 2/1981 | Hannah et al. | |
| 4,254,762 A | 3/1981 | Yoon | |
| 4,269,192 A | 5/1981 | Matsuo | |
| 4,274,771 A | 6/1981 | Nishimura | |
| 4,285,618 A | 8/1981 | Shanley | |
| 4,299,230 A | 11/1981 | Kubota | |
| 4,311,138 A | 1/1982 | Sugarman | |
| 4,319,563 A | 3/1982 | Kubota | |
| 4,356,826 A | 11/1982 | Kubota | |
| 4,386,179 A | 5/1983 | Sterling | |
| 4,414,966 A | 11/1983 | Stednitz | |
| 4,429,856 A | 2/1984 | Jackson | |
| 4,436,519 A | 3/1984 | O'Neill | |
| 4,493,444 A | 1/1985 | Deli et al. | |
| 4,498,902 A | 2/1985 | Ash et al. | |
| 4,524,805 A | 6/1985 | Hoffman | |
| 4,535,773 A | 8/1985 | Yoon | |
| 4,535,808 A | 8/1985 | Johanson et al. | |
| 4,537,593 A | 8/1985 | Alchas | |
| 4,567,882 A | 2/1986 | Heller | |
| 4,601,710 A | 7/1986 | Moll | |
| 4,750,877 A | 6/1988 | McFarlane | |
| 4,762,130 A | 8/1988 | Fogarty et al. | |
| 4,779,613 A | 10/1988 | Hashiguchi et al. | |
| 4,803,999 A | 2/1989 | Liegner | |
| 4,813,400 A | 3/1989 | Washizuka et al. | |
| 4,850,393 A | 7/1989 | Lashomb | |
| 4,895,431 A | 1/1990 | Tsujluchi et al. | |
| 4,901,142 A | 2/1990 | Ikuno et al. | |
| 4,956,143 A | 9/1990 | McFarlane | |
| 4,959,067 A | 9/1990 | Muller | |
| 4,972,827 A | 11/1990 | Kishi et al. | |
| 4,978,350 A | 12/1990 | Wagenknecht | |
| 5,017,057 A | 5/1991 | Kruygor | |
| 5,030,210 A | 7/1991 | Alchas | |
| 5,041,100 A | 8/1991 | Rowland et al. | |
| 5,057,082 A | 10/1991 | Burchette, Jr. | |
| 5,066,288 A | 11/1991 | Deniego et al. | |
| 5,098,379 A | 3/1992 | Conway | |
| 5,098,388 A | 3/1992 | Kulkashi et al. | |
| 5,104,316 A | 4/1992 | McSpadden | |
| 5,104,388 A | 4/1992 | Quackenbush | |
| 5,104,389 A | 4/1992 | Deem et al. | |
| 5,114,407 A | 5/1992 | Burbank | |
| 5,116,547 A | 5/1992 | Tsukahara et al. | |
| 5,147,376 A | 9/1992 | Pianetti | |
| 5,159,920 A | 11/1992 | Condon et al. | |
| 5,163,941 A | 11/1992 | Garth et al. | |
| 5,178,186 A | 1/1993 | Levasseur | |
| 5,186,972 A | 2/1993 | Williams et al. | |
| 5,197,955 A | 3/1993 | Stephens et al. | |
| 5,207,656 A | 5/1993 | Kranys | |
| 5,217,441 A | 6/1993 | Shichman | |
| 5,221,163 A | 6/1993 | Nishimura | |
| 5,240,397 A | 8/1993 | Fay et al. | |
| 5,246,425 A | 9/1993 | Hunsberger et al. | |
| 5,250,068 A | 10/1993 | Ideguchi et al. | |
| 5,256,149 A | 10/1993 | Banik et al. | |
| 5,258,003 A | 11/1993 | Ciaglia | |
| 5,269,316 A | 12/1993 | Spitainy | |
| 5,271,380 A | 12/1993 | Riek et al. | |
| 5,279,567 A | 1/1994 | Ciaglia et al. | |
| 5,288,290 A | 2/1994 | Brody | |
| 5,290,276 A | 3/1994 | Sewell | |
| 5,290,585 A | 3/1994 | Elton | |
| 5,300,033 A | 4/1994 | Miller | |
| 5,334,150 A | 8/1994 | Kaali | |
| 5,342,382 A | 8/1994 | Brinkerhoff | |
| 5,350,364 A | 9/1994 | Stephens et al. | |
| 5,370,624 A | 12/1994 | Edwards et al. | |
| 5,372,588 A | 12/1994 | Farley | |
| 5,374,253 A | 12/1994 | Burns, Sr. et al. | |
| 5,380,291 A | 1/1995 | Kaali | |
| 5,387,197 A | 2/1995 | Smith | |
| 5,389,077 A | 2/1995 | Melinyshin et al. | |
| 5,391,153 A | 2/1995 | Haber et al. | |
| 5,391,248 A | 2/1995 | Brain | |
| 5,392,766 A | 2/1995 | Masterson et al. | |
| 5,405,328 A | 4/1995 | Vidal et al. | |
| 5,407,427 A | 4/1995 | Zhu et al. | |
| 5,431,151 A | 7/1995 | Riek et al. | |
| 5,441,041 A | 8/1995 | Sauer et al. | |
| 5,443,484 A | 8/1995 | Kirsch et al. | |
| 5,445,615 A | 8/1995 | Yoon et al. | |
| 5,454,791 A | 10/1995 | Tovey et al. | |
| 5,480,410 A | 1/1996 | Cuschieri et al. | |
| 5,510,065 A | 4/1996 | McFarlane | |
| 5,540,711 A | 7/1996 | Kieturakis et al. | |
| 5,542,845 A | 8/1996 | Jenkins | |
| 5,549,546 A | 8/1996 | Schneider et al. | |
| 5,551,947 A | 9/1996 | Kaai | |
| 5,562,696 A | 10/1996 | Nobles et al. | |
| 5,569,291 A | 10/1996 | Privitera | |
| 5,569,292 A | 10/1996 | Scwemberger et al. | |
| 5,577,993 A | 11/1996 | Zhu et al. | |
| 5,591,186 A | 1/1997 | Wurster et al. | |
| 5,591,192 A | 1/1997 | Privitera et al. | |
| 5,593,402 A | 1/1997 | Patrick | |
| 5,603,720 A | 2/1997 | Kieturakis | |
| 5,609,562 A | 3/1997 | Kaali | |
| 5,609,604 A | 3/1997 | Schwemberger et al. | |
| 5,613,954 A | 3/1997 | Nelson et al. | |
| 5,622,462 A | 4/1997 | Gakhar et al. | |

(56) References Cited

U.S. PATENT DOCUMENTS

| | | | |
|---|---|---|---|
| 5,630,805 A | 5/1997 | Ternamian | |
| 5,634,908 A * | 6/1997 | Loomas | 604/167.06 |
| 5,658,236 A | 8/1997 | Sauer | |
| 5,662,615 A | 9/1997 | Blake, III | |
| 5,662,673 A | 9/1997 | Kieturakis | |
| 5,676,611 A | 10/1997 | Foster | |
| 5,685,820 A | 11/1997 | Riek et al. | |
| 5,695,462 A | 12/1997 | Sutcu et al. | |
| 5,697,947 A | 12/1997 | Wolf | |
| 5,720,730 A | 2/1998 | Blake, III | |
| 5,720,761 A | 2/1998 | Kaali | |
| 5,735,867 A | 4/1998 | Golser et al. | |
| 5,738,628 A | 4/1998 | Sierocuk | |
| 5,743,881 A | 4/1998 | Demco | |
| 5,746,734 A | 5/1998 | Domandy, Jr. et al. | |
| 5,752,970 A | 5/1998 | Yoon et al. | |
| 5,759,185 A | 6/1998 | Grinberg | |
| 5,779,697 A | 7/1998 | Glowa et al. | |
| 5,779,967 A | 7/1998 | Hull | |
| 5,785,693 A | 7/1998 | Halning | |
| 5,792,112 A | 8/1998 | Hart et al. | |
| 5,797,888 A | 8/1998 | Yoon et al. | |
| 5,797,944 A | 8/1998 | Nobeles et al. | |
| 5,817,061 A | 10/1998 | Goodwin et al. | |
| 5,817,062 A * | 10/1998 | Flom et al. | 604/174 |
| 5,836,957 A | 11/1998 | Shulz | |
| 5,842,971 A | 12/1998 | Yoon | |
| 5,860,996 A | 1/1999 | Urban et al. | |
| 5,871,474 A | 2/1999 | Hermann et al. | |
| 5,876,202 A | 3/1999 | Berlin | |
| 5,884,639 A | 3/1999 | Chen | |
| 5,891,013 A | 4/1999 | Thompson | |
| 5,893,865 A | 4/1999 | Swindle | |
| 5,904,699 A | 5/1999 | Schwemberger et al. | |
| 5,913,818 A | 6/1999 | Co et al. | |
| 5,922,351 A | 7/1999 | Daher | |
| 5,924,452 A | 7/1999 | Szpapa et al. | |
| 5,941,852 A | 8/1999 | Dunlap et al. | |
| 5,957,884 A | 9/1999 | Hooven | |
| 5,957,888 A | 9/1999 | Hinchliffe | |
| 5,968,060 A | 10/1999 | Kellogg | |
| 5,976,079 A | 11/1999 | Volz et al. | |
| 5,976,168 A | 11/1999 | Chin | |
| 5,980,809 A | 11/1999 | Crain et al. | |
| 5,984,941 A | 11/1999 | Wilson | |
| 6,001,084 A | 12/1999 | Riek | |
| 6,007,481 A | 12/1999 | Riek et al. | |
| 6,019,776 A | 2/2000 | Preissman | |
| 6,024,551 A | 2/2000 | Yamaguchi | |
| 6,030,406 A | 2/2000 | Davis | |
| 6,043,310 A | 3/2000 | Liu et al. | |
| 6,053,194 A | 4/2000 | Nelson et al. | |
| 6,068,637 A | 5/2000 | Popov et al. | |
| 6,077,481 A | 6/2000 | Ichida et al. | |
| 6,092,551 A | 7/2000 | Bennett | |
| 6,168,355 B1 | 1/2001 | Wardell | |
| 6,179,528 B1 | 1/2001 | Wardell | |
| 6,203,559 B1 | 3/2001 | Davis | |
| 6,203,745 B1 | 3/2001 | Wachsmann et al. | |
| 6,221,061 B1 | 4/2001 | Engelson et al. | |
| 6,228,059 B1 | 5/2001 | Astarita | |
| 6,228,063 B1 | 5/2001 | Aboul-Hosn | |
| 6,270,484 B1 | 8/2001 | Yoon | |
| 6,302,873 B1 | 10/2001 | Moenning | |
| 6,319,266 B1 | 11/2001 | Stellon | |
| 6,355,014 B1 | 3/2002 | Zadno-Azizi et al. | |
| 6,387,043 B1 | 5/2002 | Yoon | |
| 6,462,111 B1 | 10/2002 | Singh et al. | |
| 6,468,228 B1 | 10/2002 | Topel et al. | |
| 6,478,806 B2 | 11/2002 | McFarlane | |
| 6,508,759 B1 | 1/2003 | Taylor et al. | |
| 6,520,939 B2 | 2/2003 | Lafontaine | |
| 6,656,160 B1 | 12/2003 | Taylor et al. | |
| 6,656,198 B2 | 12/2003 | Tsonton et al. | |
| 6,685,630 B2 | 2/2004 | Sauer et al. | |
| 6,764,107 B1 | 7/2004 | Obahi et al. | |
| 6,770,731 B2 | 8/2004 | Mason et al. | |
| 6,835,201 B2 | 12/2004 | O'Heeron | |
| 6,884,253 B1 | 4/2005 | McFarlane | |
| 6,887,194 B2 | 5/2005 | Hart et al. | |
| 6,902,541 B2 | 6/2005 | McNally et al. | |
| 6,939,296 B2 | 9/2005 | Ewers et al. | |
| 7,008,979 B2 | 3/2006 | Schottman et al. | |
| 7,037,303 B2 | 5/2006 | Beaufore et al. | |
| 7,056,294 B2 | 6/2006 | Khairkhahan et al. | |
| 7,056,329 B2 | 6/2006 | Kerr | |
| 7,070,586 B2 | 7/2006 | Hart et al. | |
| 7,182,752 B2 | 2/2007 | Stubbs | |
| 7,344,519 B2 | 3/2008 | Wing et al. | |
| 7,370,709 B2 | 5/2008 | Williamson, Jr. | |
| 7,470,255 B2 | 12/2008 | Sterns et al. | |
| 7,563,250 B2 | 7/2009 | Wenchell | |
| 7,686,823 B2 | 3/2010 | Pingleton et al. | |
| 7,708,713 B2 | 5/2010 | Albrecht et al. | |
| 7,758,603 B2 | 7/2010 | Taylor et al. | |
| 7,794,644 B2 | 9/2010 | Taylor et al. | |
| 7,811,253 B2 | 10/2010 | Hart et al. | |
| 7,942,862 B2 | 5/2011 | Hart et al. | |
| 7,947,058 B2 * | 5/2011 | Kahle | A61B 17/3417 604/164.06 |
| 8,007,477 B2 | 8/2011 | Johnson et al. | |
| 8,028,395 B2 | 10/2011 | Taylor et al. | |
| 8,105,285 B2 | 1/2012 | Hart et al. | |
| 8,152,828 B2 | 4/2012 | Taylor et al. | |
| 8,282,663 B2 | 10/2012 | Smith | |
| 8,317,815 B2 | 11/2012 | Mastri et al. | |
| 2002/0013597 A1 | 1/2002 | McFarlane | |
| 2002/0026207 A1 | 2/2002 | Stellon et al. | |
| 2002/0133188 A1 | 9/2002 | O'Heeron et al. | |
| 2002/0183715 A1 | 12/2002 | Mantell et al. | |
| 2002/0183775 A1 | 12/2002 | Tsonton et al. | |
| 2003/0023201 A1 | 1/2003 | Aboul-Hosn | |
| 2003/0032755 A1 | 2/2003 | Gomy et al. | |
| 2003/0059263 A1 | 3/2003 | Chen | |
| 2003/0187471 A1 | 10/2003 | Cooper | |
| 2004/0015185 A1 | 1/2004 | Ewers et al. | |
| 2004/0082969 A1 | 4/2004 | Kerr | |
| 2004/0093000 A1 | 5/2004 | Kerr | |
| 2004/0093018 A1 | 5/2004 | Johnson et al. | |
| 2004/0106942 A1 | 6/2004 | Taylor et al. | |
| 2004/0108623 A1 | 6/2004 | Deeter et al. | |
| 2004/0167559 A1 | 8/2004 | Taylor et al. | |
| 2004/0199127 A1 | 10/2004 | Jensen et al. | |
| 2004/0204671 A1 | 10/2004 | Stubbs et al. | |
| 2004/0230155 A1 | 11/2004 | Blanco et al. | |
| 2004/0230217 A1 | 11/2004 | O'Heeroon | |
| 2004/0254517 A1 | 12/2004 | Quiroz-Mercado et al. | |
| 2005/0033237 A1 | 2/2005 | Fentress et al. | |
| 2005/0033246 A1 | 2/2005 | Ahlberg et al. | |
| 2005/0038466 A1 | 2/2005 | O'Heeron et al. | |
| 2005/0059865 A1 | 3/2005 | Kahle | |
| 2005/0059934 A1 * | 3/2005 | Wenchell et al. | 604/167.01 |
| 2005/0065543 A1 | 3/2005 | Kahle et al. | |
| 2005/0070850 A1 | 3/2005 | Albrecht | |
| 2005/0070851 A1 * | 3/2005 | Thompson et al. | 604/167.03 |
| 2005/0107803 A1 | 5/2005 | Guanche | |
| 2005/0107816 A1 | 5/2005 | Pingleton et al. | |
| 2005/0113533 A1 | 5/2005 | Shaikh et al. | |
| 2005/0149094 A1 | 7/2005 | Kasahara et al. | |
| 2005/0149096 A1 | 7/2005 | Hilal et al. | |
| 2005/0159711 A1 | 7/2005 | Kathrani et al. | |
| 2005/0216028 A1 | 9/2005 | Hart et al. | |
| 2005/0227610 A1 | 10/2005 | Zukor et al. | |
| 2005/0273133 A1 | 12/2005 | Schluzas et al. | |
| 2005/0283122 A1 | 12/2005 | Nordgren | |
| 2005/0288622 A1 * | 12/2005 | Albrecht et al. | 604/23 |
| 2006/0030755 A1 | 2/2006 | Ewers et al. | |
| 2006/0041270 A1 | 2/2006 | Lenker et al. | |
| 2006/0047284 A1 | 3/2006 | Gresham | |
| 2006/0058570 A1 | 3/2006 | Rapach et al. | |
| 2006/0074374 A1 | 4/2006 | Gresham | |
| 2006/0118189 A1 | 6/2006 | Trekulve et al. | |
| 2006/0224174 A1 * | 10/2006 | Smith et al. | 606/190 |
| 2006/0264991 A1 * | 11/2006 | Johnson et al. | 606/167 |

(56) References Cited

U.S. PATENT DOCUMENTS

| | | |
|---|---|---|
| 2007/0027453 A1 | 2/2007 | Hart et al. |
| 2007/0075465 A1 | 4/2007 | Taylor et al. |
| 2007/0088277 A1 | 4/2007 | McGinley |
| 2007/0239108 A1 | 10/2007 | Albrecht et al. |
| 2008/0065021 A1 | 3/2008 | Jenkins et al. |
| 2008/0086074 A1 | 4/2008 | Taylor et al. |
| 2008/0086093 A1 | 4/2008 | Steppe et al. |
| 2009/0137943 A1 | 5/2009 | Stearns et al. |
| 2010/0025045 A1 | 2/2010 | Lake et al. |

FOREIGN PATENT DOCUMENTS

| | | |
|---|---|---|
| DE | 0365049 | 12/1922 |
| DE | 1616107 | 4/1971 |
| DE | 2218901 | 10/1973 |
| DE | 2538758 | 3/1977 |
| DE | 29 29 233 | 1/1980 |
| DE | 2929233 | 1/1980 |
| DE | 2922239 | 12/1980 |
| DE | 4020956 | 1/1991 |
| DE | 4133073 | 4/1992 |
| DE | 4035146 | 5/1992 |
| DE | 4116648 | 11/1992 |
| DE | 29521431 | 4/1997 |
| DE | 19541041 | 5/1997 |
| DE | 19718086 | 11/1998 |
| DE | 19819432 | 11/1999 |
| EP | 0135364 | 3/1985 |
| EP | 0312787 | 4/1989 |
| EP | 0347140 | 12/1989 |
| EP | 0369936 | 5/1990 |
| EP | 0369937 | 5/1990 |
| EP | 0474124 | 3/1992 |
| EP | 0548612 | 6/1993 |
| EP | 0556056 | 8/1993 |
| EP | 0724864 | 8/1996 |
| EP | 1582158 | 10/2005 |
| EP | 1 733 707 | 12/2006 |
| EP | 2229897 | 9/2010 |
| EP | 2233090 | 9/2010 |
| FR | 1370580 | 8/1964 |
| GB | 2 124 970 | 2/1984 |
| GB | 186 005 | 9/1992 |
| GB | 2 313 316 | 11/1997 |
| JP | 408127661 | 5/1996 |
| JP | 2001-137253 | 5/2001 |
| SU | 0942730 | 7/1982 |
| SU | 1328658 | 8/1987 |
| SU | 1329769 | 8/1987 |
| WO | WO 93/25148 | 12/1993 |
| WO | WO 96/01132 | 1/1996 |
| WO | WO 96/10361 | 4/1996 |
| WO | WO 97/40758 | 11/1997 |
| WO | WO 98/33536 | 8/1998 |
| WO | WO 99/02089 | 1/1999 |
| WO | WO 99/15084 | 4/1999 |
| WO | WO 00/18306 | 4/2000 |
| WO | WO 00/54648 | 9/2000 |
| WO | WO 01/08563 | 2/2001 |
| WO | WO 02/01998 | 1/2002 |
| WO | WO 02/34108 | 5/2002 |
| WO | WO 03/020140 | 3/2003 |
| WO | WO 03/026512 | 4/2003 |
| WO | WO 03/032819 | 4/2003 |
| WO | WO 03/096879 | 11/2003 |
| WO | WO 2004/037097 | 5/2004 |
| WO | WO 2004/093699 | 11/2004 |
| WO | WO 2005/063134 | 7/2005 |
| WO | WO 2007/093957 | 8/2007 |

OTHER PUBLICATIONS

Co-Pending U.S. Appl. No. 10/489,403, filed Mar. 11, 2004; Title: Bladeless Obturator.

Co-Pending U.S. Appl. No. 10/514,313, filed Nov. 12, 2004; Title: Blunt Tip Obturator.

Co-Pending U.S. Appl. No. 11/170,567, filed Jun. 29, 2005; Title: Insufflating Optical Surgical Instrument.

Co-Pending U.S. Appl. No. 10/745,262, filed Dec. 23, 2003, Title: Catheter With Conduit Traversing Tip.

Co-Pending U.S. Appl. No. 10/956,167, filed Oct. 3, 2003; Title: Bladeless Optical Obturator.

Co-Pending U.S. Appl. No. 10/346,846, filed Jan. 17, 2003; Title: Surgical Access Apparatus and Method.

Co-Pending U.S. Appl. No. 10/805,864, filed Mar. 22, 2004; Title: Surgical Access Port and Method.

Co-Pending U.S. Appl. No. 11/868,883, filed Oct. 8, 20007; Title Visual Insufflation Port.

International Searching Authority, The International Search Report and Written Opinion of the International Searching Authority for International Application No. PCT/US2007/080724 mailed Apr. 16, 2008.

International Preliminary Report of Patentability for international application No. PCT/US2005/022716, mailed Jan. 18, 2007.

European Patent Office, The International Search Report and Written Opinion for International Application No. PCT/US2005/022716, mailed Nov. 22, 2005.

European Patent Office, European Search Report for European Application No. 12187933, titled "Insufflating Optical Surgical Instrument", dated Nov. 20, 2012.

European Patent Office, European Search Report for European Application No. 12187929, titled "Insufflating Optical Surgical Instrument", dated Nov. 20, 2012.

U.S. Appl. No. 10/745,262, filed Dec. 23, 2003; Title: "Catheter With Conduit Traversing Tip" (abandoned).

Co-Pending U.S. Appl. No. 12/750,372, filed Mar. 30, 2010, title: "Bladeless Obturator".

Co-Pending U.S. Appl. No. 11/549,872, filed Oct. 16, 2006, title: "Surgical Devices, Systems and Methods Thereof Having Gel Material, Gel Coatings, or Gel Lubricants".

Co-Pending U.S. Appl. No. 13/565,972, filed Aug. 3, 2012, title: "Bladeless Optical Obturator".

Co-Pending U.S. Appl. No. 13/356,260, filed Jan. 23, 2012, title: "Insufflating Optical Surgical Instrument".

Co-Pending U.S. Appl. No. 13/078,750, filed Apr. 1, 2011 title "Surgical Access Apparatus and Method".

Co-Pending U.S. Appl. No. 12/569,652, filed Sep. 29, 2009; title "First-Entry Trocar System".

Co-Pending U.S. Appl. No. 12/359,964, filed Jan. 26, 2009, title: "Insufflating Access System".

Co-Pending U.S. Appl. No. 13/462,330, filed May 2, 2012, title: "Low-Profile Surgical Universal Access Port".

Co-Pending U.S. Appl. No. 13/411,244, filed Mar. 2, 2012, title: "Blunt Tip Obturator".

Co-Pending U.S. Appl. No. 13/586,825, filed Aug. 15, 2012, title: "Blunt Tip Obturator".

Co-Pending U.S. Appl. No. 11/868,883, filed Oct. 8, 2007; Title: "Visual Insufflation Port".

International Bureau of WIPO, International Preliminary Report on Patentability for International Application No. PCT/US04/032346, dated May 20, 2008.

International Bureau of WIPO, International Preliminary Report on Patentability for International Application No. PCT/US2005/022716 mailed Nov. 22, 2005.

International Bureau of WIPO, International Preliminary Report on Patentability for International Application No. PCT/US2006/060013, mailed Apr. 24, 2008.

International Bureau of WIPO, The International Preliminary Report on Patentability for International Application No. PCT/US2009/058792, titled First Entry Trocar System, dated Mar. 29, 2011.

International Bureau of WIPO, The International Preliminary Report on Patentability for International Application No. PCT/US2007/080724, titled "Visual Insufflation Port", dated Apr. 7, 2009.

International Bureau of WIPO, The International Preliminary Report on Patentability for International Application No. PCT/US2009/32026, titled "Insufflating Access System", dated Jul. 27, 2010.

(56) References Cited

OTHER PUBLICATIONS

International Bureau of WIPO, The International Preliminary Report on Patentability for International Application No. PCT/US2004/000695, titled "Surgical Access Apparatus and Method", dated Jul. 22, 2005.

International Bureau of WIPO, The International Preliminary Report on Patentability for International Application No. PCT/US2004/04883, titled "Surgical Access Apparatus and Method", dated Sep. 9, 2005.

International Searching Authority, International Search Report and Written Opinion for International Application No. PCT/US2004/000695, titled "Surgical Access Apparatus and Method", mailed Jan. 12, 2005.

International Searching Authority, International Search Report and Written Opinion for International Application No. PCT/US2004/04883, titled "Surgical Access Apparatus and Method", mailed Mar. 31, 2005.

International Searching Authority, International Search Report and Written Opinion for International Application No. PCT/US2002/06759, titled "Bladeless Obturator", mailed Jul. 12, 2002.

International Searching Authority, International Search Report Written Opinion for International Application No. PCT/US2005/022716, titled "Insufflating Optical Surgical Instrument", mailed Nov. 22, 2005.

International Searching Authority, International Search Report and Written Opinion for International Application No. PCT/US04/32346, titled Bladeless Optical Obturator, mailed May 20, 2008.

International Searching Authority, International Search Report and Written Opinion for International Application No. PCT/US2009/32026, titled "Insufflating Access System", mailed Mar. 23, 2009.

International Searching Authority, International Search Report and Written Opinion for International Application No. PCT/US2007/080724, titled "Visual Insufflation Port", mailed Apr. 16, 2008.

International Searching Authority/US, International Search Report and the Written Opinion of the International Searching Authority dated May 27, 2009, for International Application No. PCT/US2009/037863, titled "Instrument Seal with Inverting Shroud", mailed May 27, 2009.

The International Searching Authority, The International Search Report and the Written Opinion for International Application No. PCT/US2009/058792, titled "First Entry Trocar System", mailed Dec. 23, 2009,.

International Searching Authority, International Search Report and Written Opinion for International Application No. PCT/US2012/036119, title "Low-Profile Surgical Universal Access Port", mailed Nov. 7, 2012.

European Patent Office, Supplementary European Search Report for European Patent Application No. EP 02706494.8, titled "Bladeless Obturator", dated Jun. 24, 2008.

European Patent Office, Supplementary European Search Report for European Patent Application No. EP 03753017.7, titled "Blunt Tip Obturator", dated Nov. 21, 2008.

European Patent Office, Supplementary European Search Report for European Patent Application No. EP 047122378, titled "Surgical Access Apparatus and Method", dated May 19, 2008.

European Patent Office, Supplementary European Search Report for European Patent Application No. EP 07843973.4, titled "Visual Insufflation Port" dated Oct. 4, 2008.

European Patent Office, Supplementary European Search Report for European Patent Application No. EP 04793965.7, titled "Bladeless Optical Obturator", dated Apr. 16, 2010.

European Patent Office, Supplementary European Search Report for European Patent Application No. EP 11154547.1, titled "Blunt Tip Obturator", dated Mar. 22, 2011.

European Patent Office, European Search Report for European Application No. 11191191.3, titled "Bladeless Obturator" dated Feb. 29, 2012.

European Patent Office, European Search Report for European Application No. 11191179.8, titled "Bladeless Obturtor", dated Feb. 21, 2012.

European Patent Office, European Search Report for European Application No. 11191193.9, titled "Bladeless Obturator", dated Mar. 5, 2012.

European Patent Office, European Search Report for European Application No. 11191187.1, titled Bladeless Obturator, dated Feb. 23, 2012.

European Patent Office, European Search Report for European Application No. 11191184.8, titled "Bladeless Obturator", dated Feb. 23, 2012.

European Patent Office, European Search Report for European Application No. 11191189.7, titled "Bladeless Obturator", dated Feb. 24, 2012.

European Patent Office, European Search Report for European Application No. 11191175.6, titled "Bladeless Obturator", dated Feb. 21, 2012.

European Patent Office, European Search Report for European Application No. 047017314, titled "Surgical Access Apparatus and Method", dated Mar. 30, 2007.

Taut, Inc., Adapt-Asymmetrical Dilating Access Port, Geneva Illinois.

Karl Storz, The Karl Storz Ternamian EndoTIP (TM) System, date: Aug. 27, 2001.

Karl Storz, Zerocart Trocar with eccentric tip, Recklinghausen, Germany, date Mar. 7, 2001.

Ethicon Endo-Surgery, Inc., ENDOPATH Minimally Invasive Access, date: 2001.

European Patent Office, Invitation to Pay Additional Fees for International Application No. PCT/US2012/036119, entitled "Low-Profile Surgical Universal Access Port", mailed Jul. 13, 2012.

European Patent Office, European Extended Search Report for European Application No. 09703532.3, titled "Insufflating Access System", dated Jan. 21, 2014.

* cited by examiner

INSUFFLATING ACCESS SYSTEM

CROSS-REFERENCE TO RELATED APPLICATION

This application claims the benefit of U.S. Application No. 61/023,539, filed Jan. 25, 2008, the disclosure of which is incorporated by reference.

BACKGROUND

1. Technical Field

This application is generally directed to surgical instruments, and more particularly, to a first entry, insufflating access system.

2. Description of the Related Art

In laparoscopic procedures in which a patient's abdomen is insufflated or inflated with gas, placing a device through which the abdomen is insufflated, also referred to as a first entry device, is often problematic. Because the peritoneum directly contacts the organ bed, a device puncturing the peritoneum can also damage the underlying organ bed. Placing subsequent devices is less dangerous because the insufflating the abdomen lifts the peritoneum above a gas-fill space or cavity above the organ bed, thereby reducing the risk of inadvertent damage thereto.

Several techniques are used to achieve pneumoperitoneum in laparoscopic surgery. A first technique uses a Veress needle, which is a sharp needle placed blindly through the abdominal wall into the abdominal cavity. An insufflation gas, for example, $CO_2$, is then pumped through the hollow Veress needle and into the abdominal cavity, thereby insufflating the peritoneal cavity. The Veress needle technique, also known as a controlled stab, is capable of damaging organs such as the intestinal tract. The technique provides little or no feedback to the surgeon that any damage to an anatomic structure has occurred.

A second technique is known as the Hassan technique in which a surgeon performs a mini-laparotomy through the abdominal layers into the abdominal cavity, through which a trocar is inserted and the abdomen insufflated. The Hassan technique is a cut-down technique that results in larger abdominal defects and increased patient scarring. The technique is also difficult to perform on obese patients with very thick abdominal walls.

In a third technique, the surgeon places a trocar optically, visualizing the abdominal layers as the trocar is placed through the abdominal wall through a laparoscope disposed within the obturator of the trocar. The tip of the obturator can penetrate about 2 cm (about 0.75") into the organ bed of the abdominal cavity when placing the cannula and establishing pneumoperitoneum.

In a fourth technique, the abdominal layers are visualized while the trocar is advanced though the abdominal wall. As soon as the tip of the obturator punctures the peritoneum, gas is pumped through the trocar system into the abdominal cavity through vent holes disposed at the tip of the obturator. The fourth technique uses a vacuum release, which causes the organs to fall away from the abdominal wall, thereby creating a space in the abdominal cavity for the obturator tip. Accordingly, the abdominal cavity can be inflated with minimal penetration into the space. As soon as the tip of the obturator punctures the peritoneum, gas enters the abdominal cavity through the vent holes in the tip of the obturator, thereby reducing the negative pressure caused by the surgeon's lifting of the abdominal wall, and in turn, creating a space above the organ bed into which the trocar system is fully inserted into the cavity. A seal is disposed within the obturator that provides a gas tight seal both with and without the laparoscope in place. The vent holes at the tip of the obturator allow moisture and tissue to enter the obturator, however, which obscure the field of view within the obturator tip. Gas flowing directly past the laparoscope within the obturator can cool the laparoscope, thereby fogging of the lens thereof.

SUMMARY OF THE INVENTION

Systems, devices, and methods permit insufflation of a body cavity prior to the insertion of a cannula into the body cavity. Some embodiments of an access system comprise an obturator, a trocar, and a fluid flow channel. The access system has a closed configuration, in which a distal end of the access system is fluidly isolated from the fluid flow channel, and an open configuration, in which the distal end of the access system is fluidly connected to the fluid flow channel, thereby permitting fluid flow, for example, an insufflation gas into a body cavity.

Accordingly, some embodiments provide an insufflating surgical access system and a method for insufflating a body cavity using the insufflating surgical access system. Some embodiments of the insufflating surgical access system comprise: a trocar comprising: a proximal end and a distal end; a trocar seal assembly disposed at the proximal end of the trocar, the trocar seal assembly comprising an instrument seal; an elongate cannula disposed at the distal end of the trocar, the cannula comprising a tubular wall defining a lumen, an open proximal end, and an open distal end; an access channel defining a longitudinal axis, extending through the trocar seal assembly and the lumen of the cannula, from the proximal end of the trocar to the distal end of the trocar; a fluid port disposed at the proximal end of the trocar; and a fluid flow seal disposed in the access channel; an obturator comprising: an elongate body comprising a proximal end and a distal end; a tissue penetrating tip disposed at the distal end; and a handle disposed at the proximal end, wherein the obturator is slidably insertable into the proximal end of the access channel, and the tip of the obturator extends out of the distal, open end of the cannula when fully inserted therethrough; and a fluid flow channel fluidly connected to the fluid port of the trocar, and extending to a distal end of the insufflating access system. The obturator in the access channel has a closed position, in which the body of the obturator sealing contacts the fluid flow seal, thereby preventing gas flow through the fluid flow channel, and an open position, in which the body of the obturator does not sealing contact the fluid flow seal, thereby allowing fluid flow through the fluid flow channel.

In some embodiments, the trocar seal assembly further comprises a zero seal.

In some embodiments, the distal end of the cannula comprises an angled tip.

In some embodiments, the fluid port is disposed on the trocar seal assembly.

In some embodiments, the fluid flow seal is integrated with a cannula tip disposed at the distal end of the cannula. In some embodiments, the fluid flow seal is disposed proximal of the distal end of the cannula. In some embodiments, the fluid flow seal is substantially perpendicular to the longitudinal axis of the axis channel. In some embodiments, the fluid flow seal is not perpendicular to the longitudinal axis of the axis channel.

In some embodiments, the obturator further comprises an instrument well open at a proximal end of the obturator, extending longitudinally through the body of the obturator, terminating at the tip of the obturator, and dimensioned to receive a laparoscope therein, wherein at least a portion of the tip of the obturator is transparent. Some embodiments further comprise a laparoscope.

In some embodiments, the fluid flow channel comprises a space defined by the lumen of the cannula and the body of the obturator. In some embodiments, the fluid flow channel comprises an instrument well disposed in the body of the obturator. In some embodiments, the fluid flow channel comprises at least one proximal opening and at least one distal opening disposed in the body of the obturator. In some embodiments, the fluid flow channel comprises a slot disposed in the body of the obturator.

In some embodiments, in the closed position, the obturator is displaced distally in the access channel compared with the open position. In some embodiments, in the closed position, the obturator is displaced proximally in the access channel compared with the open position. In some embodiments, in the closed position, the obturator is rotated in the access channel compared with the open position.

Some embodiments of the method for insufflating a body cavity comprise: positioning the obturator in the closed position; fluidly connecting the fluid port with a source of insufflation gas; positioning the tissue penetrating tip at a desired position; advancing the tissue penetrating tip through a body wall until the tip enters a body cavity; and positioning the obturator in the open position, fluidly connecting the fluid port with the body cavity through the fluid flow channel, thereby insufflating the body cavity.

Some embodiments further comprise visually monitoring the position of the penetrating tip through a laparoscope.

Some embodiments provide an insufflating surgical access system comprising: a trocar comprising: a proximal end and a distal end; a trocar seal assembly disposed at the proximal end of the trocar, the trocar seal assembly comprising an instrument seal; an elongate cannula disposed at the distal end of the trocar, the cannula comprising a tubular wall defining a lumen, an open proximal end, and an open distal end; an access channel defining a longitudinal axis, extending through the trocar seal assembly and the lumen of the cannula, from the proximal end of the trocar to the distal end of the trocar; a fluid port disposed at the proximal end of the trocar; an obturator comprising: an elongate body comprising a proximal end and a distal end; a tissue penetrating tip disposed at the distal end; and a handle disposed at the proximal end, wherein the obturator is slidably insertable into the proximal end of the access channel, and the tip of the obturator extends out of the distal, open end of the cannula when fully inserted therethrough; and a gas flow channel fluidly connected to the fluid port of the trocar, and extending to a distal end of the insufflating access system; and means for modulating gas flow through the gas flow channel.

DETAILED DESCRIPTION OF CERTAIN EMBODIMENTS

Figure 1A:
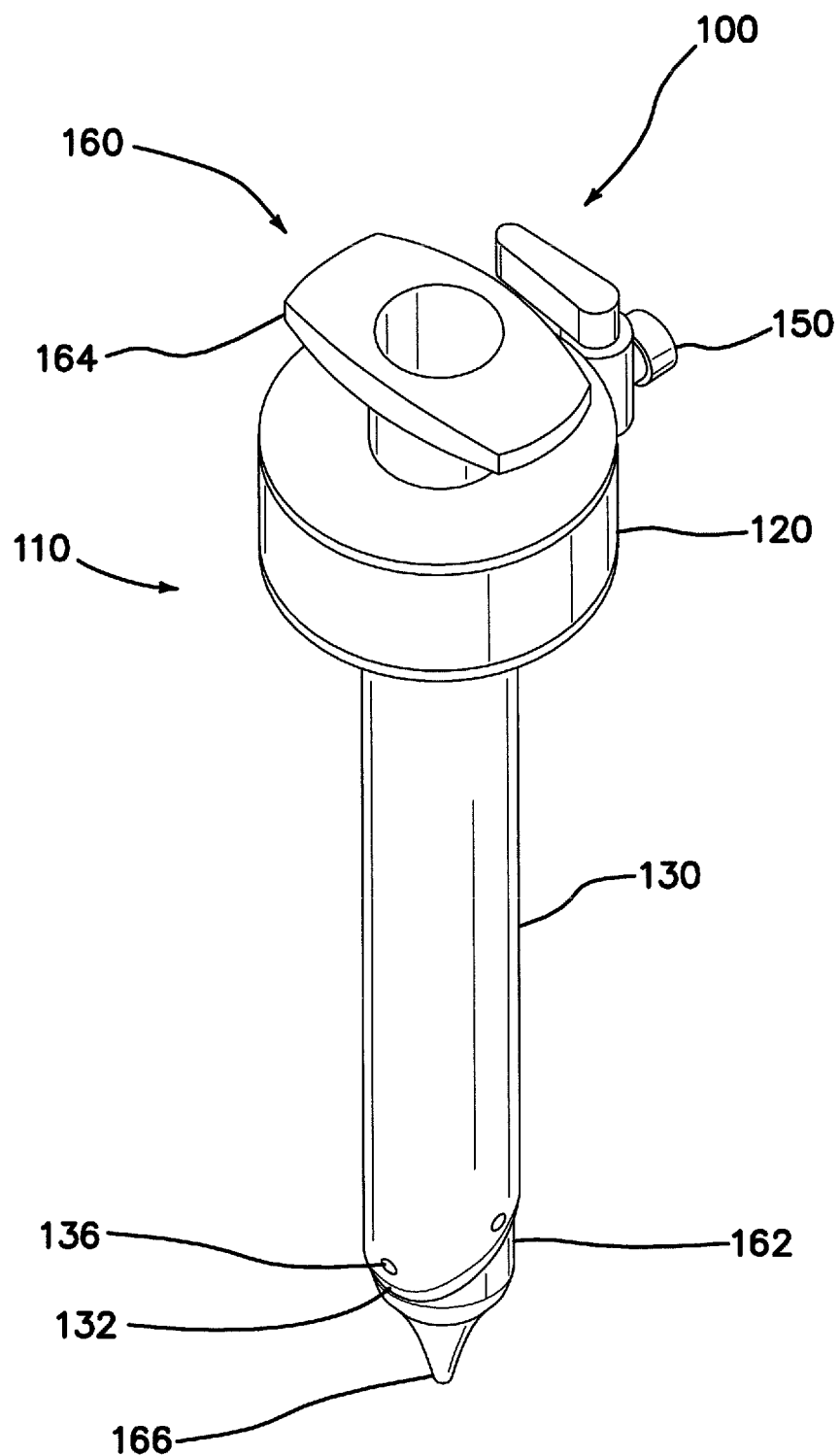
FIG. 1A is a perspective view of an embodiment of an insufflating access system.

FIG. 1A is a perspective view of an embodiment of an insufflating access system 100 comprising a trocar 110 and an obturator 160 slidably insertable into the trocar 110. The insufflating access system 100 also comprises a fluid flow channel, which is discussed in greater detail below. The trocar 110 and obturator 160 comprise suitable biologically compatible materials.

Figure 1B:
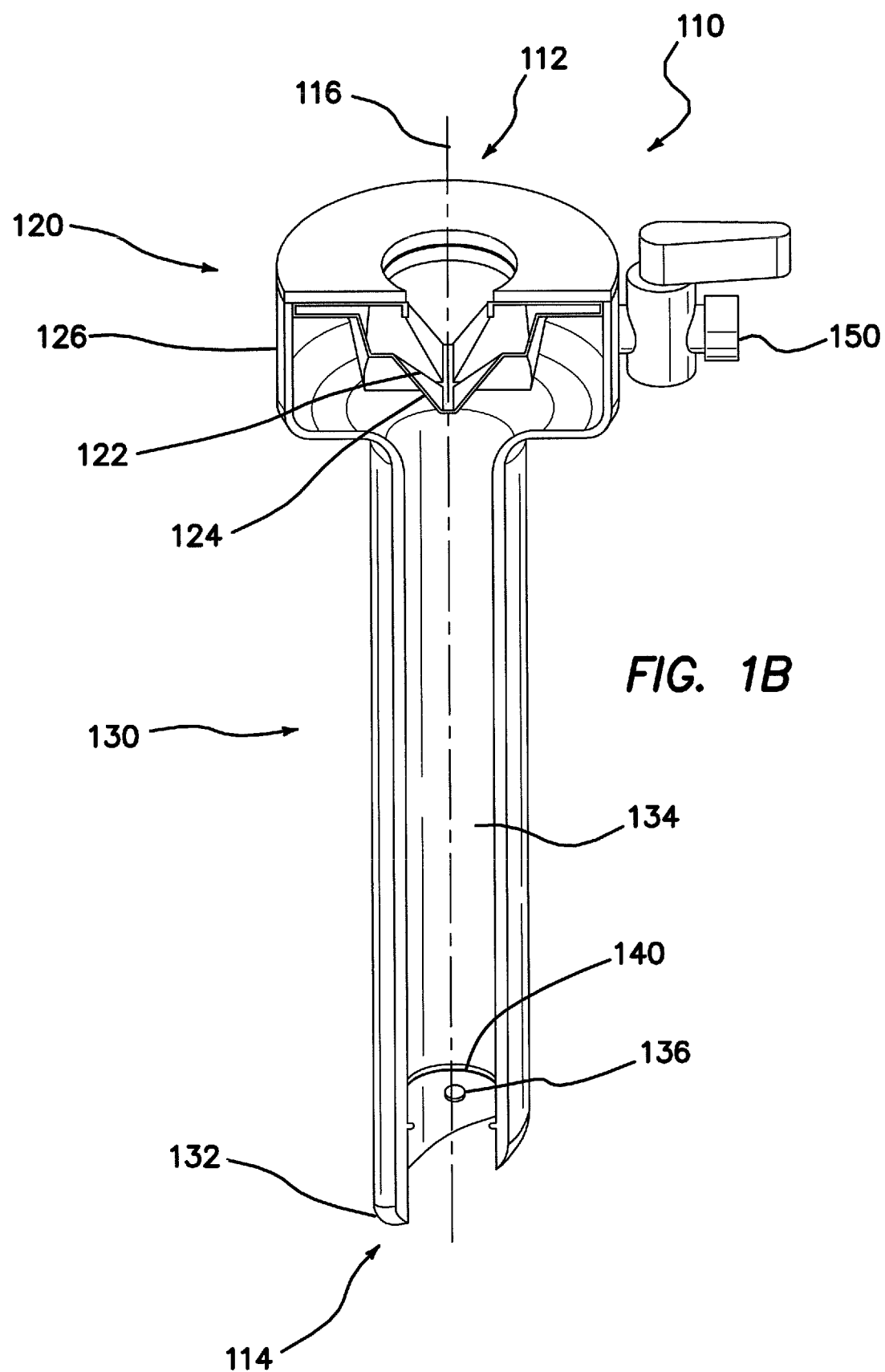
FIG. 1B is a perspective cutaway view of a trocar of the insufflating access system illustrated in FIG. 1A.
Figure 1C:
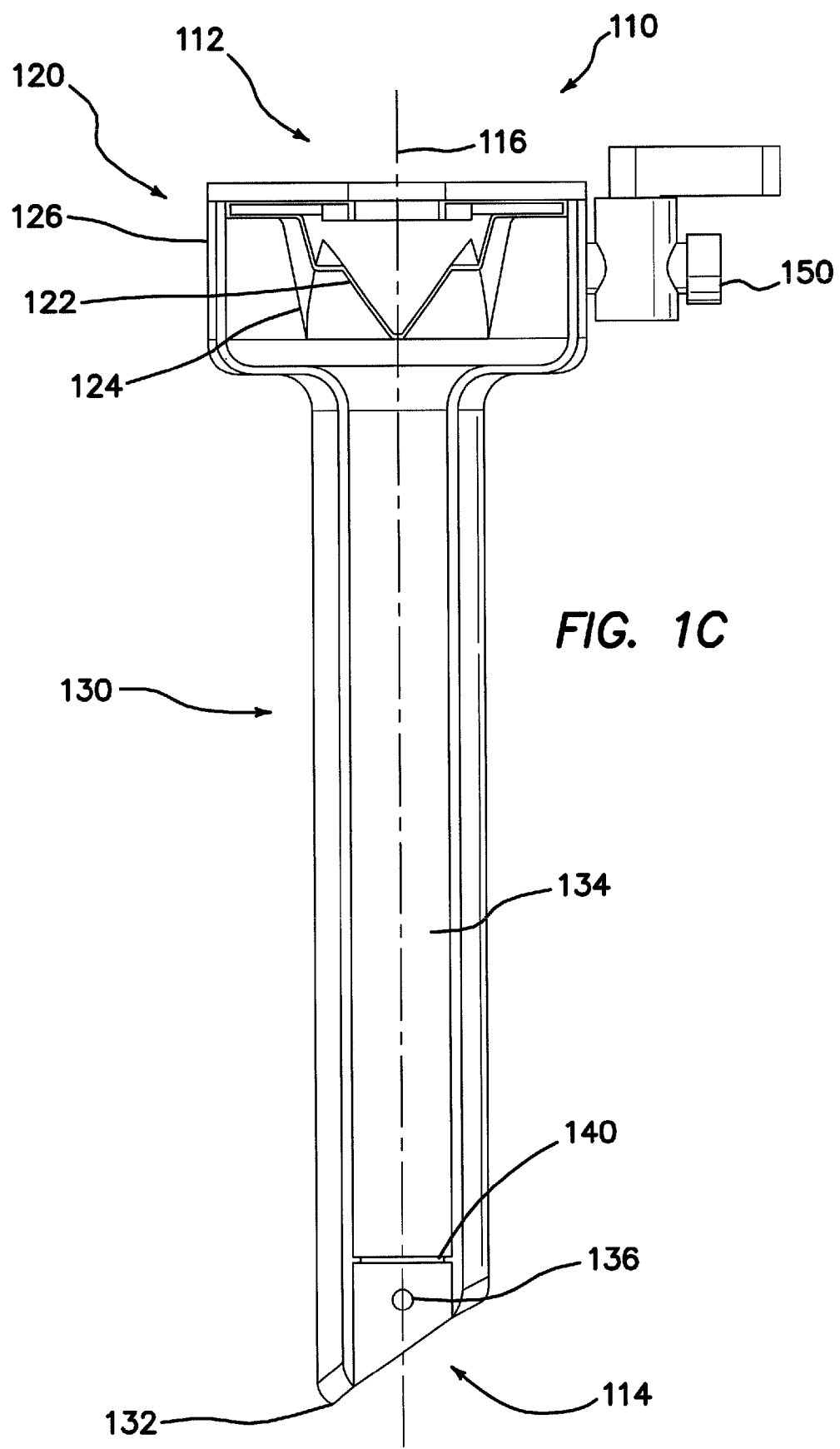
FIG. 1C is a side cutaway view of the trocar illustrated in FIG. 1B.

FIG. 1B is a perspective cutaway view and FIG. 1C is a partial side cross section of the trocar 110. The trocar 110 comprises a proximal end 112 and a distal end 114. A trocar seal assembly 120 is disposed at the proximal end 112 of the trocar, and an elongate cannula 130 extends from the trocar seal assembly 120 and is disposed at the distal end 114 of the trocar. An access channel 116 extends through the trocar seal assembly 120 and the cannula 130, from the proximal end 112 to the distal end 114 of the trocar. The access channel 116 defines a longitudinal axis. In some embodiments, the trocar seal assembly 120 and the cannula 130 are integrated, while in other embodiments, the trocar seal assembly 120 and the cannula 130 are separate components, and in some embodiments, releasably coupled.

In the illustrated embodiment, the trocar seal assembly 120 comprises a first seal 122 and a second seal 124 disposed on the access channel 116 within a trocar seal housing 126. The first seal 122 is an instrument seal, which forms a substantially fluid tight seal with an instrument extending therethrough, thereby preventing fluid from escaping from the proximal end 112 of the trocar. In some embodiments, the first seal 122 comprises a septum seal. The second seal 124 is a zero seal, which forms a fluid tight seal with no instrument extending therethrough, preventing fluid from escaping from the proximal end 112 of the trocar. In some embodiments, the second seal 124 comprises a duckbill valve, a double duckbill valve, and/or a flap valve. The second seal 124 is optional in some embodiments. For example, in some embodiments, the first seal 122 provides both an instrument seal and a zero seal, for example, a valve comprising a gel material. Other embodiments do not comprise a zero seal. In some embodiments, the first seal 122 and the second seal 124 comprise an elastomer, for example rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene (Neoprene®), perfluoroelastomer (Kalrez®), and the like.

The cannula 130 comprises a proximal end, at which the trocar seal assembly 120 is disposed, and a distal end terminating in a tip 132. In the illustrated embodiment, the tip 132 of the cannula is angled with a beveled edge. The angled tip 132 facilitates insertion through tissue. In other embodiments, the tip 132 is not angled. The cannula 130 comprises a hollow tube open at the proximal and the distal ends. The hollow tube defines a lumen 134, through which the access channel 116 extends. One or more optional vents 136 perforate the cannula 130 at or near the distal end thereof. In the illustrated embodiment, the cannula 130 has a generally circular cross section, although those skilled in the art will understand that other embodiments have other suitable cross sections, for example, oval, elliptical, diamond, square, polygonal, and the like.

A fluid flow seal 140 is disposed within the lumen of the cannula 130, on an inner wall of the hollow tube. The fluid flow seal 140 is positioned, dimensioned, and configured for sealing contacting the body 162 of the obturator, as discussed in greater detail below. In the illustrated embodiment, the fluid flow seal 140 is disposed near the tip 132 or distal end of the cannula. The fluid flow seal 140 is substantially normal or perpendicular to the longitudinal axis of the trocar 110, and consequently, is generally circular in the illustrated embodiment. In other embodiments, the fluid flow seal 140 is disposed at another location. For example, in some embodiments, the fluid flow seal 140 is disposed at or integrated with the tip 132 of the cannula, or spaced adjacent to or just slightly inward from the tip 132 at the distal-most end. In some of these embodiments in which the tip 132 is not perpendicular to the longitudinal axis of the trocar 110, the fluid flow seal 140 also subtends a non-normal angle with the longitudinal axis, and consequently, is elliptical or oval rather than circular. In some embodiments, the fluid flow seal 140 and the tip 132 subtend about the same angle with the longitudinal axis, while in other embodiments, the fluid flow seal 140 and the tip 132 subtend different angles with the longitudinal axis. Some embodiments of the fluid flow seal 140 comprise a plurality of sub-seals, which are disposed at about the same location in some embodiments, and disposed in a plurality of locations in other embodiments. The fluid flow seal 140 comprises a suitable elastomer for example, at least one of rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene (Neoprene®), perfluoroelastomer (Kalrez®), and the like.

A fluid port 150 is disposed on the housing 126 of the trocar seal assembly, fluidly connected with the access channel 116 distal of the first 122 and second 124 seals. The fluid port 150 comprises a stopcock in the illustrated embodiment, and terminates in a fitting that permits coupling to a fluid and/or suction source, for example, a Luer fitting. In other embodiments, the fluid port 150 has another location, for example, on the cannula 130 or the obturator 160. Embodiments of the fluid port 150 are useful for introducing and/or venting an insufflation gas, for example, carbon dioxide, therethrough. Other fluids are introduced and/or vented in other embodiments.

The trocar 110 is typically manufactured in a range of sizes to accommodate instruments of different diameters, for example, up to about 5 mm, up to about 8 mm, up to about 11 mm, up to about 12 mm, or up to about 15 mm. Embodiments of the trocar 110 have working cannula lengths of about 55 mm, about 75 mm, about 100 mm, or about 150 mm.

Figure 1D:
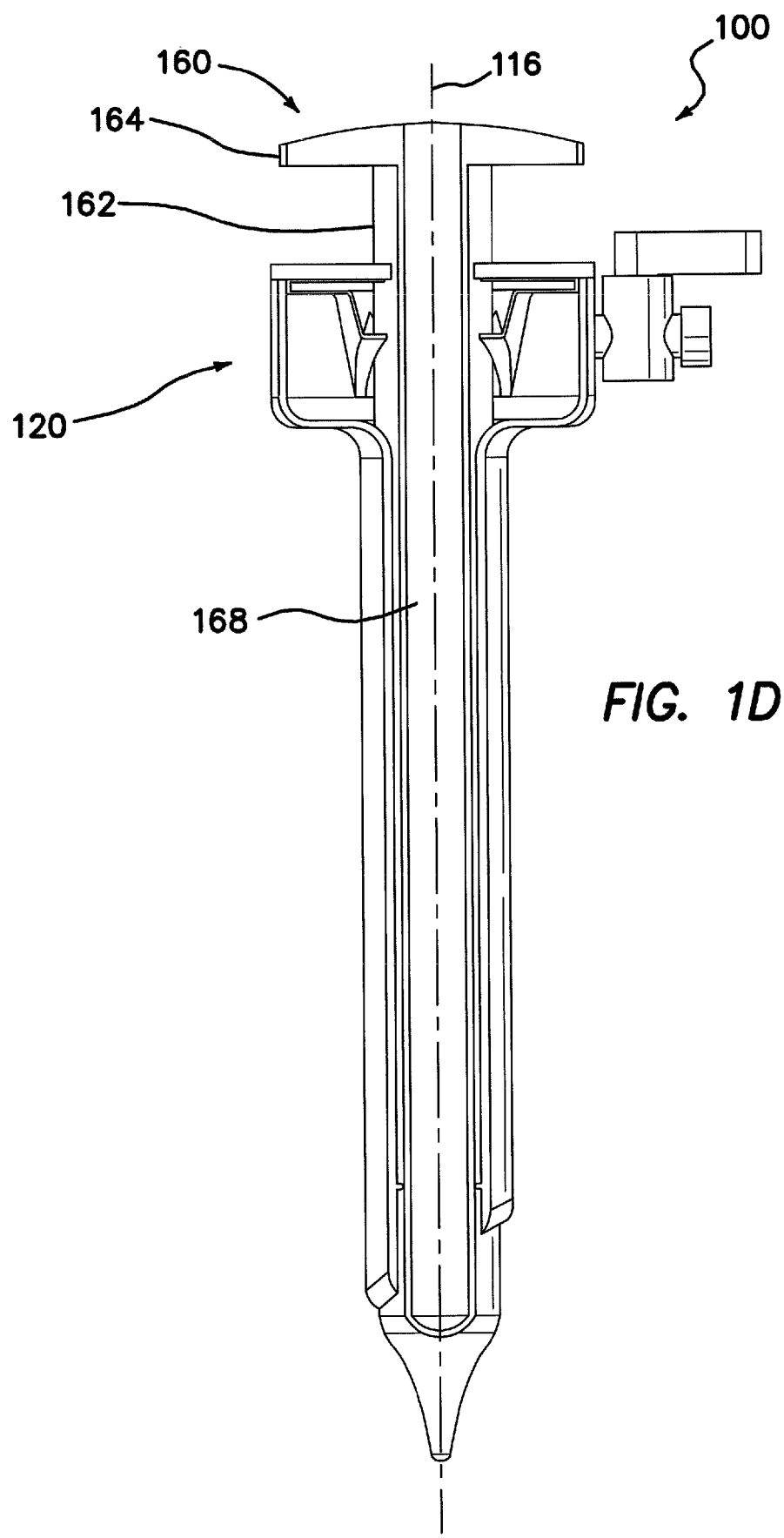
FIG. 1D is a side cutaway view of the insufflating access system illustrated in FIG. 1A in the closed configuration.

As best seen in FIG. 1D, which is a side cutaway view of the insufflating access system 100, the obturator 160 comprises an elongate body 162 comprising a proximal end terminating in a handle 164 and a distal end terminating in a tissue penetrating tip 166. A diameter of the tip 166 converges from a proximal end to a distal end thereof. The body 162 and tip 166 of obturator is slidably insertable into and removable from the access channel 116 through the proximal end of the trocar 110. In a fully inserted configuration, the tip 166 of the obturator extends out of the distal end or tip 132 of the cannula 130. The first seal 122 of the trocar seal assembly forms an instrument seal with the body 162 of the cannula, thereby substantially preventing fluid leaking from the proximal end of the access channel 116. In the illustrated embodiment, the body 162 comprises a hollow, instrument well 168, which is open at the handle 162 at the proximal end of the obturator, and which extends to the tip 166 of the obturator. The instrument well 168 is dimensioned to receive a laparoscope through the proximal opening thereof. When fully inserted, an end of the laparoscope extends through the body 162 of the obturator into or proximal to the tip 166. In the illustrated embodiment, the tip 166 comprises at least a transparent or windowed portion through which the laparoscope images tissue proximal to the tip 166, for example, for monitoring the position of the tip 166 during the insertion of the access system 100 into a body cavity. Some embodiments of the tip 166 comprise markers or another type of visually enhancing or facilitating features, which assist in viewing the tissue and body cavity, and thus, traversal of the tip 166 through the body. In some embodiments, the laparoscope is fully inserted in the instrument well 168, thereby preventing or reducing fogging thereof. Accordingly, some embodiments comprise at least one of a distal laparoscope seal, membrane, or lock in that provides at least one of holding the laparoscope in a fully or nearly fully inserted position, preventing or reducing fogging, and preventing or reducing other types of interference of the viewing area of the laparoscope.

Figure 1E:
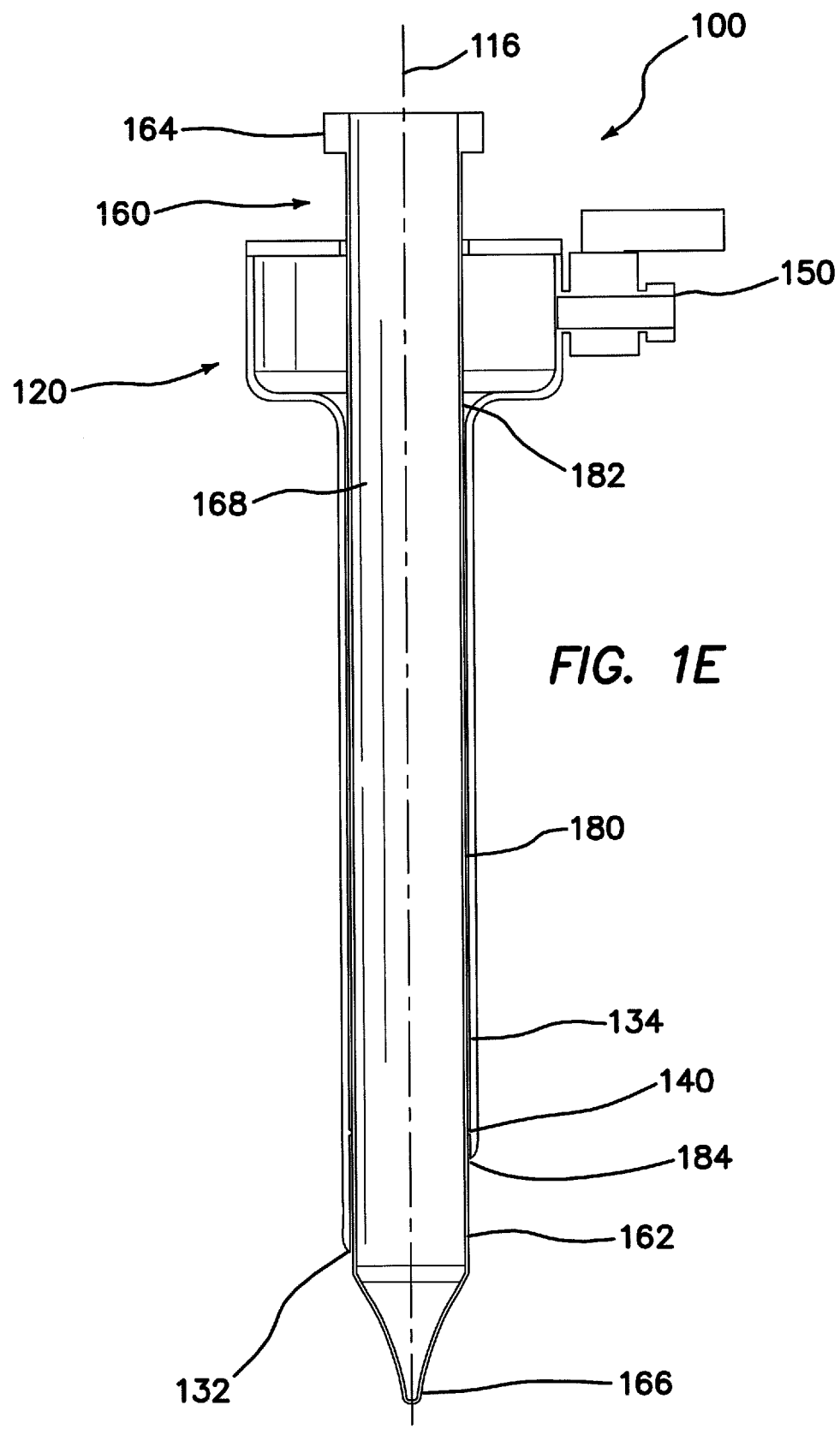
FIG. 1E is a side cross-sectional view of the insufflating access system illustrated in FIG. 1A in a closed configuration.
Figure 1F:
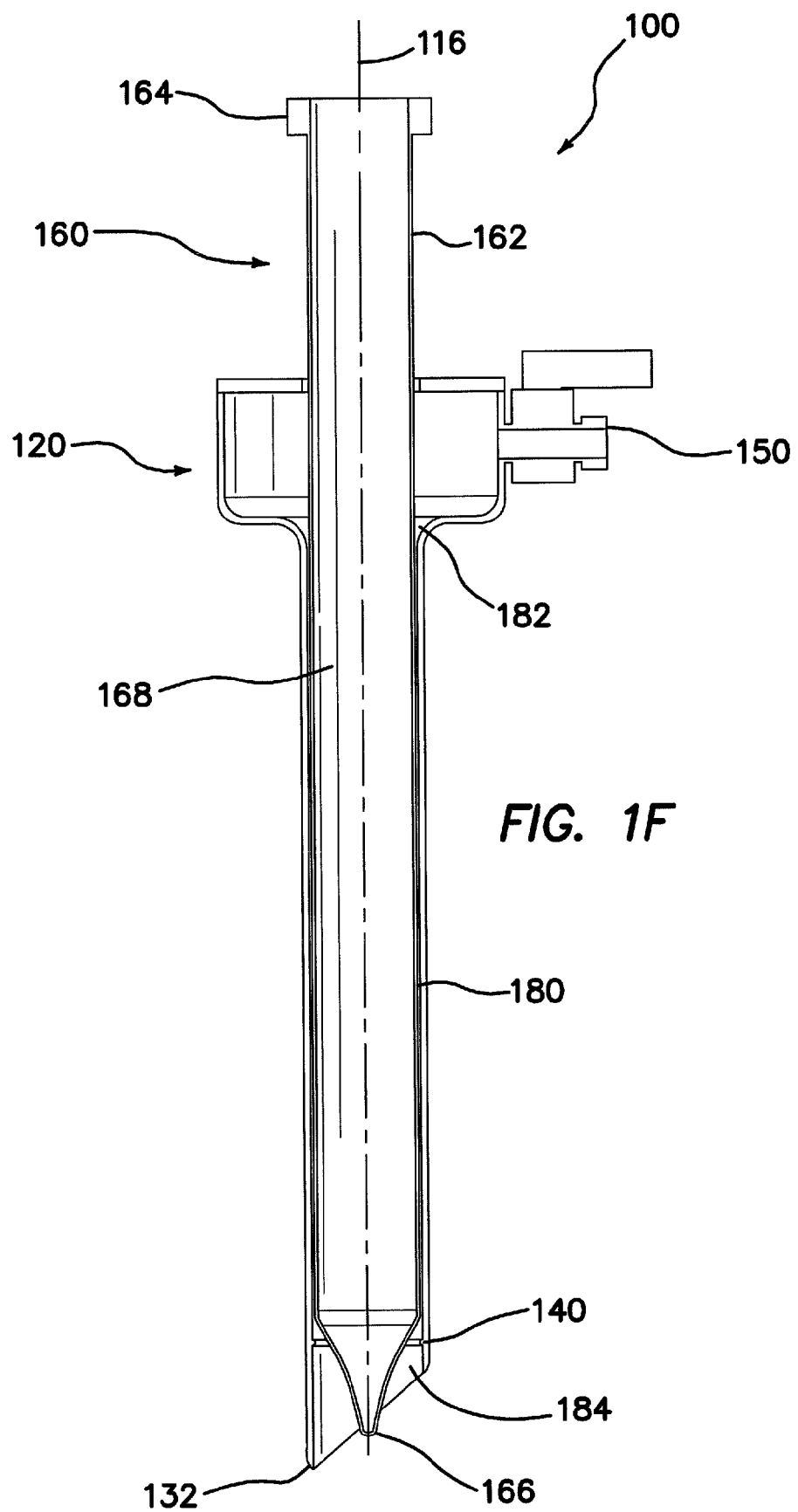
FIG. 1F is a cross-sectional view of the insufflating access system illustrated in FIG. 1A in an open configuration.

FIG. 1E is a side cross section of the insufflating access system 100 in a closed configuration and FIG. 1F is a side cross section of the insufflating access system 100 in an open configuration. The lumen 134 of the cannula and the body 162 of the obturator together define a fluid flow channel 180 therebetween, which extends longitudinally in the access channel 116. A proximal end 182 of the fluid flow channel is fluidly connected to the fluid port 150. A distal end 184 of the fluid flow channel extends to the distal end of the access system 100, which in the illustrated embodiment, comprises the tip 132 of the cannula. In the illustrated embodiment, the lumen 134 of the cannula and the body 162 of the obturator are both generally circular and define a fluid flow channel 180 with a generally annular cross section. In other embodiments, cross-sectional shapes of the lumen 134 of the cannula and the body 162 of the obturator are different from each other, and the cross section of the fluid flow channel 180 has another shape.

A size of a space or gap between the tip 166 of the obturator and the tip 132 of the cannula is selected to prevent or reduce coring of tissue as the access system is advanced. In some embodiments, the gap between the tip 166 of the obturator and the tip 132 of the cannula provides sufficient gas flow for insufflation, which is discussed in greater detail below. In some embodiments, a gap between the body 162 of the obturator and the lumen 134 of the cannula is not uniform longitudinally, for example, wider at the proximal end 112 and narrower at the distal end 116.

In the closed configuration illustrated in FIG. 1E, the tip 166 of the obturator extends from the tip 132 of the cannula in a configuration suitable for inserting the access system 100 through a body wall and into a body cavity. The position of the obturator 160 in this configuration is referred to as a closed position. In the closed configuration, the fluid flow seal 140 sealing contacts the body 162 of the obturator, thereby cooperating therewith to prevent fluid flow through the fluid flow channel 180, from the fluid port 150, and out through the tip 132 of the cannula. Accordingly, the fluid port 150 is not fluidly connected with the distal end of the fluid flow channel 184.

In the open configuration illustrated in FIG. 1F, the obturator 160 is partially withdrawn from access channel 116, that is translated proximally along the longitudinal axis compared with the configuration illustrated in FIG. 1E. The position of the obturator 160 in this configuration is referred to as an open position. In the illustrated embodiment, the body 162 of the obturator is proximal of the fluid flow seal 140, and consequently, does not make contact and form a seal therewith. Accordingly, in the open configuration, the distal end 184 of the fluid flow channel is fluidly connected with the fluid port 150. In some embodiments, the fluid flow seal 140 contacts a portion of the body 162 of the obturator in the open configuration, but does not sealing contact therewith. For example, in some embodiments, at least one of the fluid flow seal 140, and a transition between the body 162 and tip 166 of obturator are not normal or perpendicular to the longitudinal axis. In some of these embodiments, in some positions of the obturator 160 in the access channel, the body 162 of the obturator contacts only a portion of the fluid flow seal 140 rather than the entire sealing surface thereof, and consequently, does not form a seal therewith.

Some embodiments of the access system 100 comprise an indicator of the configuration thereof. For example, some embodiments comprise indicia on the obturator 160 and/or the trocar 110 that indicate the position of the obturator 160 in the open and/or closed position. Some embodiments comprise an audio and/or visual indicator of fluid flow through the fluid flow channel 180 and/or fluid port 150, for example, a spinning disk, a spinning ball, a lamp, a whistle, and/or an alarm.

Some embodiments comprise one or more mechanical features that indicate the state of and/or lock the access system 100 into at least one of the open configuration and the closed configuration, for example, detents, latches, stops, and the like.

Figure 2A:
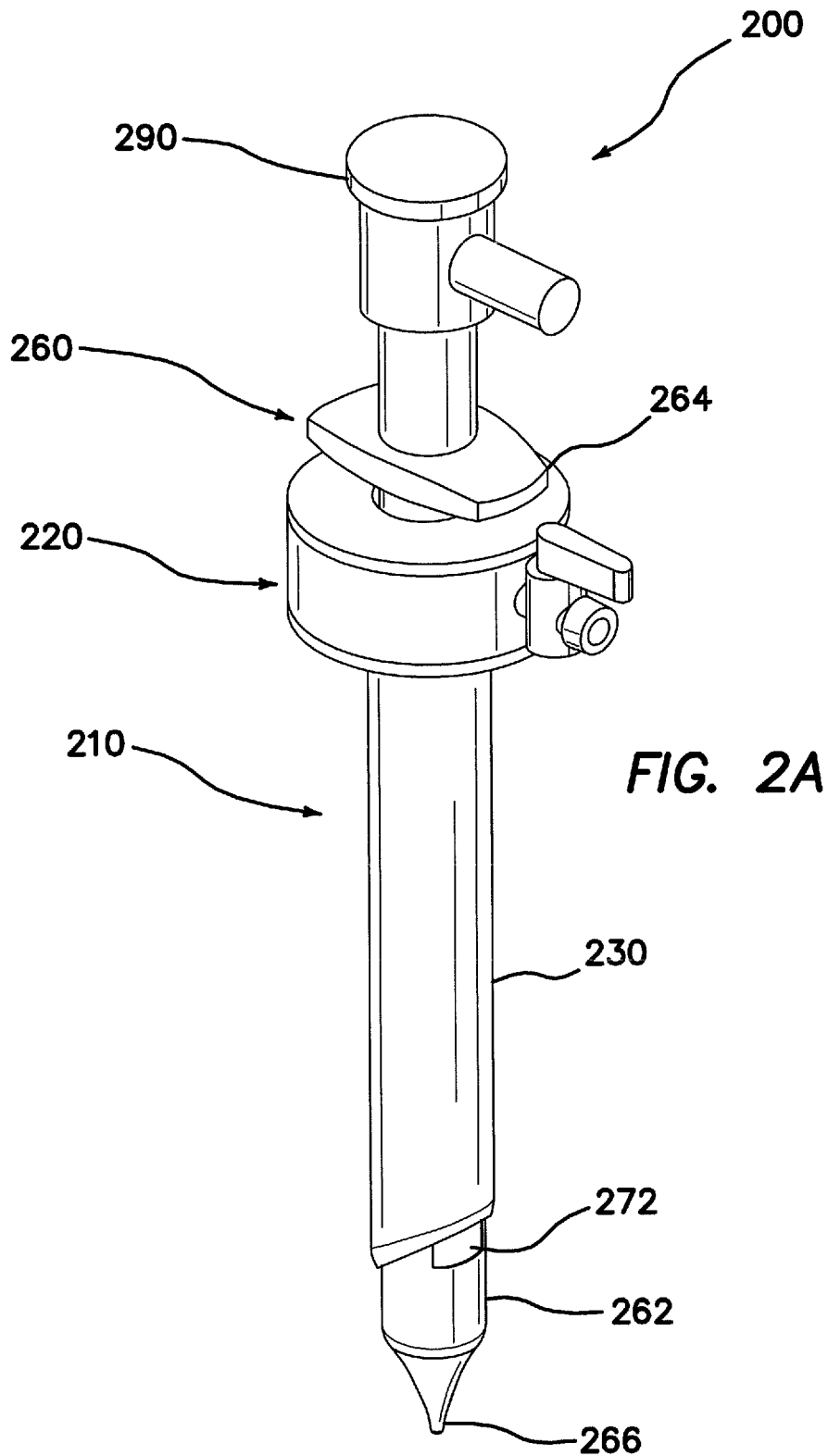
FIG. 2A is a perspective view of another embodiment of an insufflating access system.
Figure 2B:
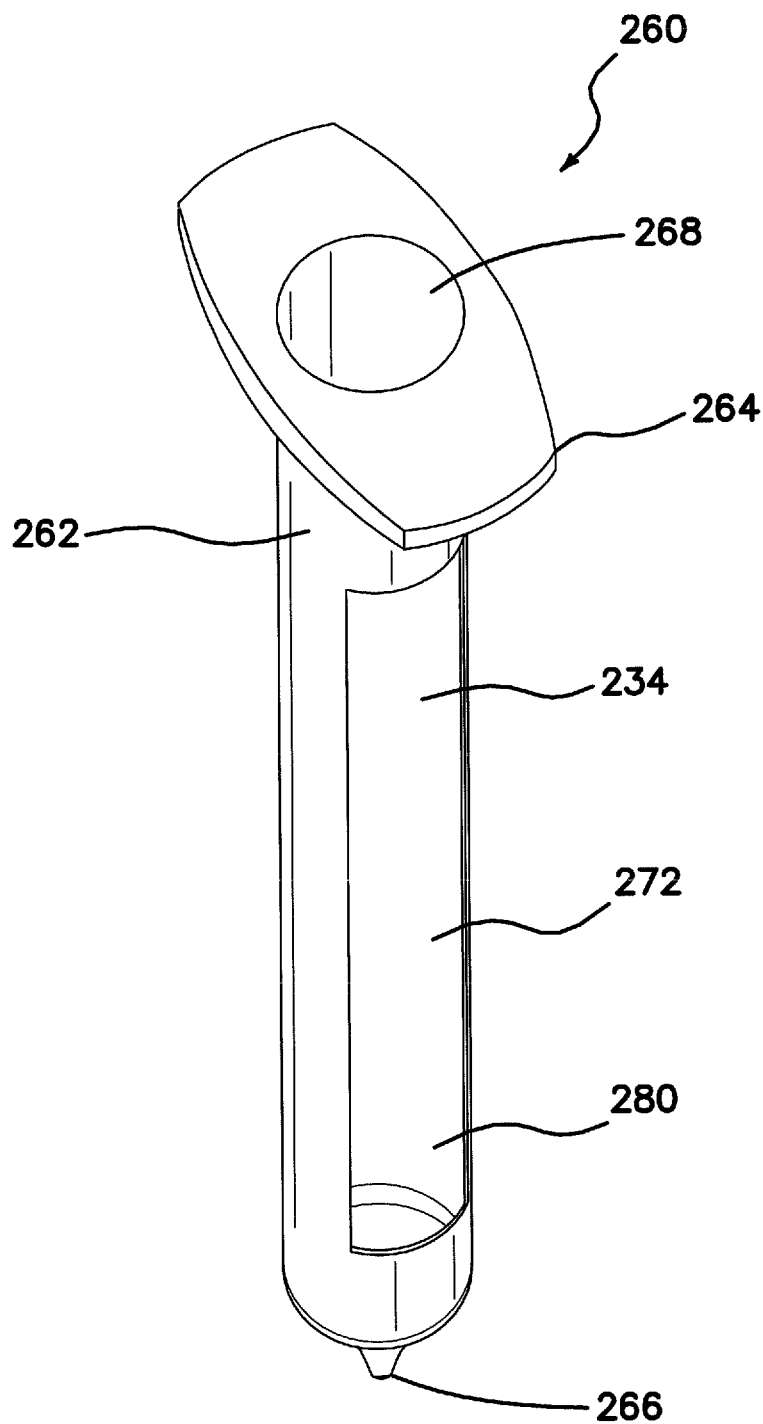
FIG. 2B is a perspective view of an embodiment of an obturator from the insufflating access system illustrated in FIG. 2A.

FIG. 2A is a perspective view of another embodiment of an insufflating access system 200 generally similar to the embodiment illustrated in FIGS. 1A-1F, comprising a trocar 210, an obturator 260 inserted in the trocar 210, and a laparoscope 290 inserted into the obturator 260. FIG. 2B is a perspective view of an embodiment of the obturator 260, which is similar to the embodiment of the obturator 160 described above, and comprises an elongate body 262, a handle 264 disposed at the proximal end, a tip 266 disposed at the distal end, and an instrument well 268 extending longitudinally from an opening in the handle 264 at the proximal end of the obturator to the tip 266 at the distal end thereof.

The obturator 260 further comprises a slot 272 that extends longitudinally on the body 262 thereof. As will be apparent from the description below, the slot 272 incorporates the instrument well 268 into the fluid flow channel 280 in the illustrated embodiment. Because the fluid flow channel 280 comprising the instrument well 268 has a larger cross-sectional area compared with the fluid flow channel 180 of embodiment illustrated in FIGS. 1A-1F, embodiments of the access system 200 exhibit increased fluid flow. A proximal end of the slot 272 is positioned such that the slot 272 does not interfere with the instrument seal between the body 262 and the trocar seal assembly 220 when the obturator 260 is in the open position or the closed position. A distal end of the slot 272 is positioned such that fluid does not flow from the slot 272 in the closed configuration, that is, the distal end of the slot 272 is fluidly isolated from the distal end of the access system 200. The open configuration permits fluid flow from the distal end of the slot 272, that is, the distal end of the slot 272 is fluidly connected to the distal end of the access system 200. In the illustrated embodiment, the slot 272 perforates the body 262 of the obturator into the instrument well 268. Accordingly, the illustrated embodiment comprises a seal between the proximal end of the obturator 260 and the laparoscope 290, thereby preventing or reducing fluid flow therefrom. The seal is disposed on at least one of the laparoscope 290 and the obturator 260. In some embodiments, the slot 272 does not perforate the body 262 of the obturator, for example, comprising one or more longitudinal grooves disposed on an outer surface of the body 262. The seal between the proximal end of the obturator 260 and the laparoscope 190 is optional in these embodiments. Some embodiments of the fluid flow channel 280 comprise one or more longitudinal grooves disposed on an inner wall of the cannula 230.

Figure 2C:
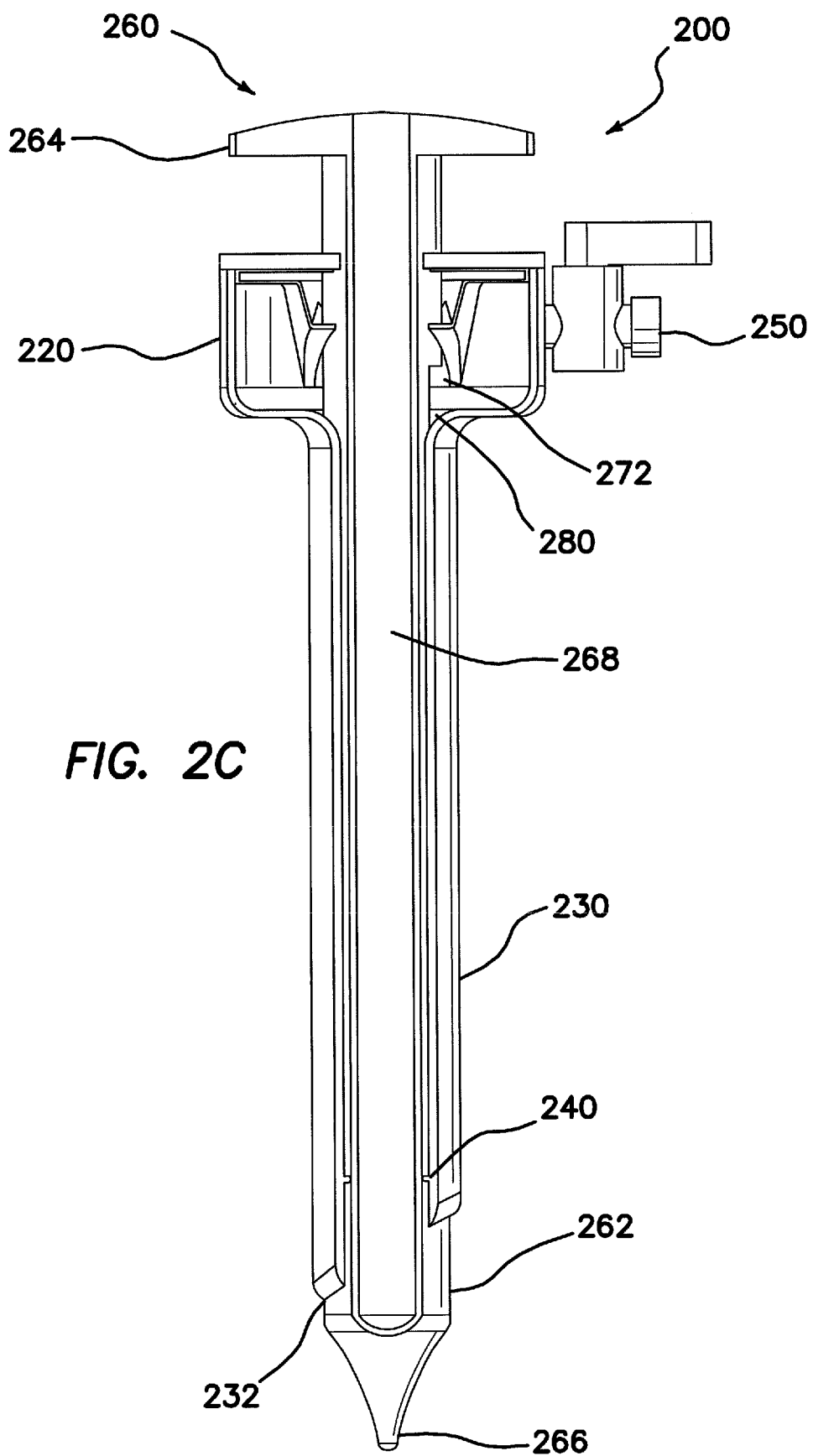
FIG. 2C is a side cutaway view of an embodiment of the insufflating access system illustrated in FIG. 2A in a closed configuration.

FIG. 2C is a side cutaway view of an embodiment of the insufflating access system illustrated in FIG. 2A in a closed configuration. In the closed position, the obturator 260 is inserted into the access channel of the trocar 210 with the tip 266 extending from the tip 232 of the cannula in a tissue penetrating position. The proximal end of the slot 272 is disposed below the instrument seal of the seal assembly 220, in fluid communication with the fluid port 250. The distal end of the slot 272 is disposed proximal to the fluid channel seal 240, which seals with the body 262 of the obturator, thereby fluidly isolating the slot 272 from the tip 232 of the cannula and the distal end of the access system 200.

Figure 2D:
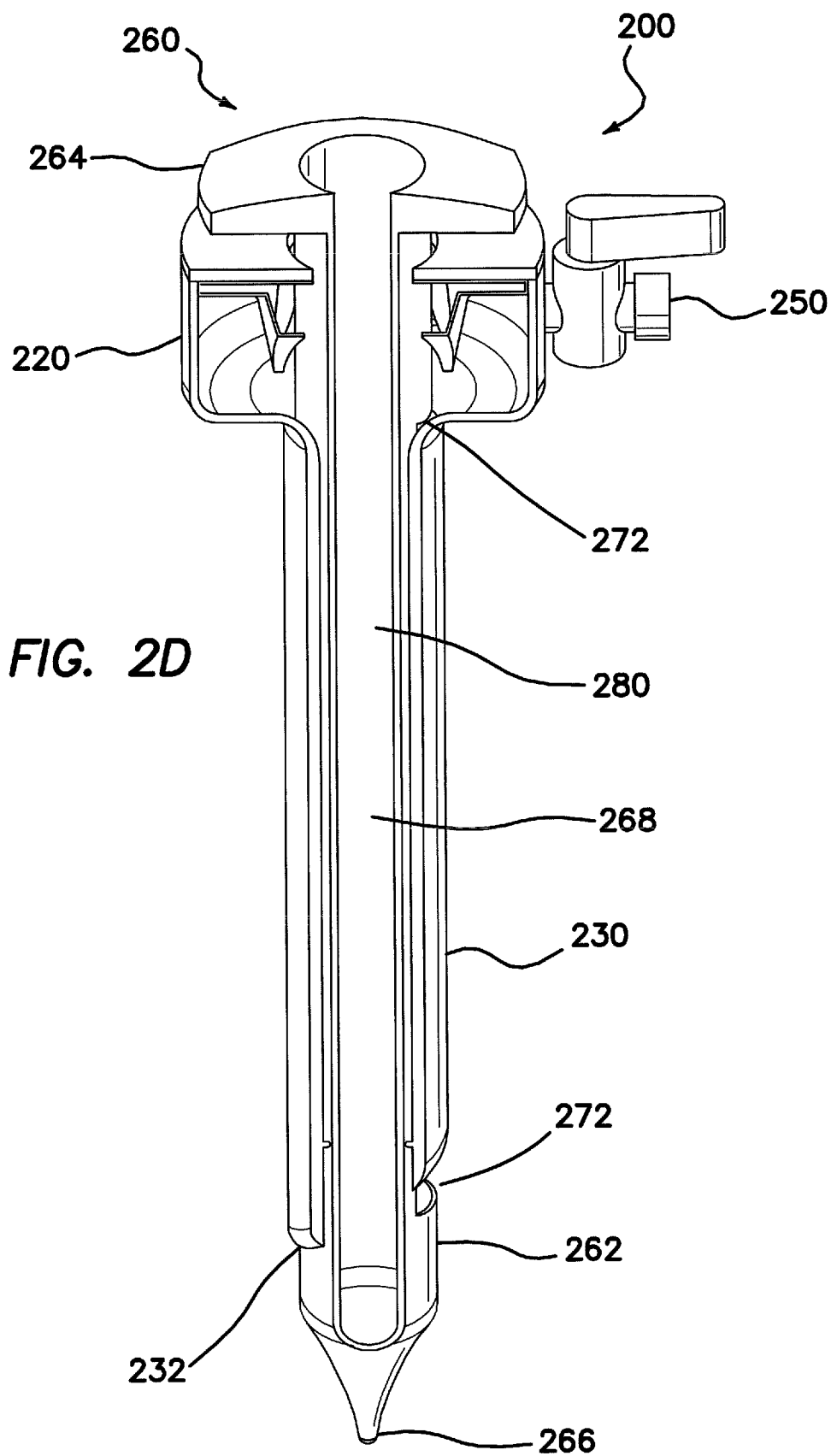
FIG. 2D is a side cutaway view of the embodiment of the insufflating access system illustrated in FIG. 2C in an open configuration.

FIG. 2D is a side cutaway view of the embodiment of the insufflating access system illustrated in FIG. 2C in an open configuration in which the obturator 260 is advanced distally in the access channel, for example, using the handle 264, thereby advancing the distal end of the slot 272 past the fluid channel seal 240, and thereby releasing the seal between the body 262 of the obturator and the fluid channel seal 240. In the illustrated embodiment, the slot 272 has about the same length as the cannula 230, extending from about the position of the fluid inlet to past a proximal portion of the angled tip 232 of the cannula, with which the slot 272 is aligned. Accordingly, alignment of the distal end of the slot 272 with the proximal portion of the angled tip 232 exposes the distal end of the slot 272, thereby providing a fluid flow channel 280 that permits insufflation gas to exit directly out the slot 272 and into the body cavity. In some embodiments, the obturator 260 and trocar 210 are keyed or otherwise configured to prevent rotation therebetween, thereby locking the slot 272 in the exposed condition when the access system 200 is in the open configuration. Those skilled in the art will understand that some embodiments in which the slot 272 is rotated relative to the configuration illustrated in FIG. 2D such that the distal end of the slot 272 and the proximal portion of the angled tip 232 are not aligned, also permit fluid flow therethrough, but at reduced flow rates.

In other embodiments, the access system 200 has an open configuration, as illustrated in FIG. 2A, with a fluid flow seal 240 disposed in the cannula 230 at or near the angled tip 232 thereof. As discussed above, in some of these embodiments, the fluid flow seal 240 subtends the same or a similar angle as the tip 232. Rotating the obturator 260 positions the entirety of the slot 272 within the cannula 230, proximal of the fluid flow seal 240, thereby converts the open configuration to the closed configuration in which the distal end of the slot 272 is fluidly isolated from the distal end of the access system 200, and preventing fluid flow therefrom. In some of these embodiments, rotation of the handle 264 of the obturator is restricted such that the device 200 is in the open configuration at a first limit of the rotation and in a closed configuration at a second limit thereof.

Figure 3A:
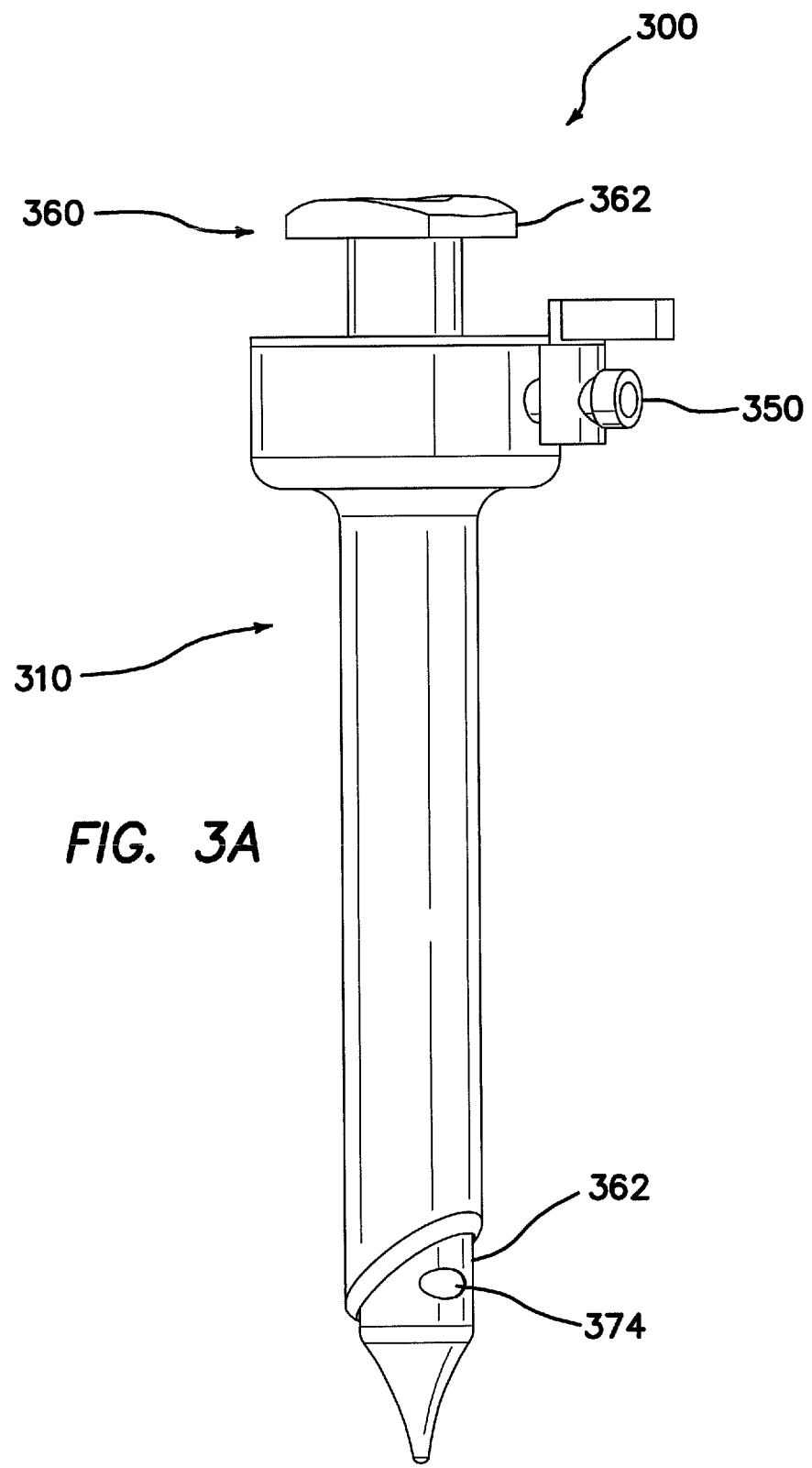
FIG. 3A is a perspective view of another embodiment of an insufflating access system in an open configuration.
Figure 3B:
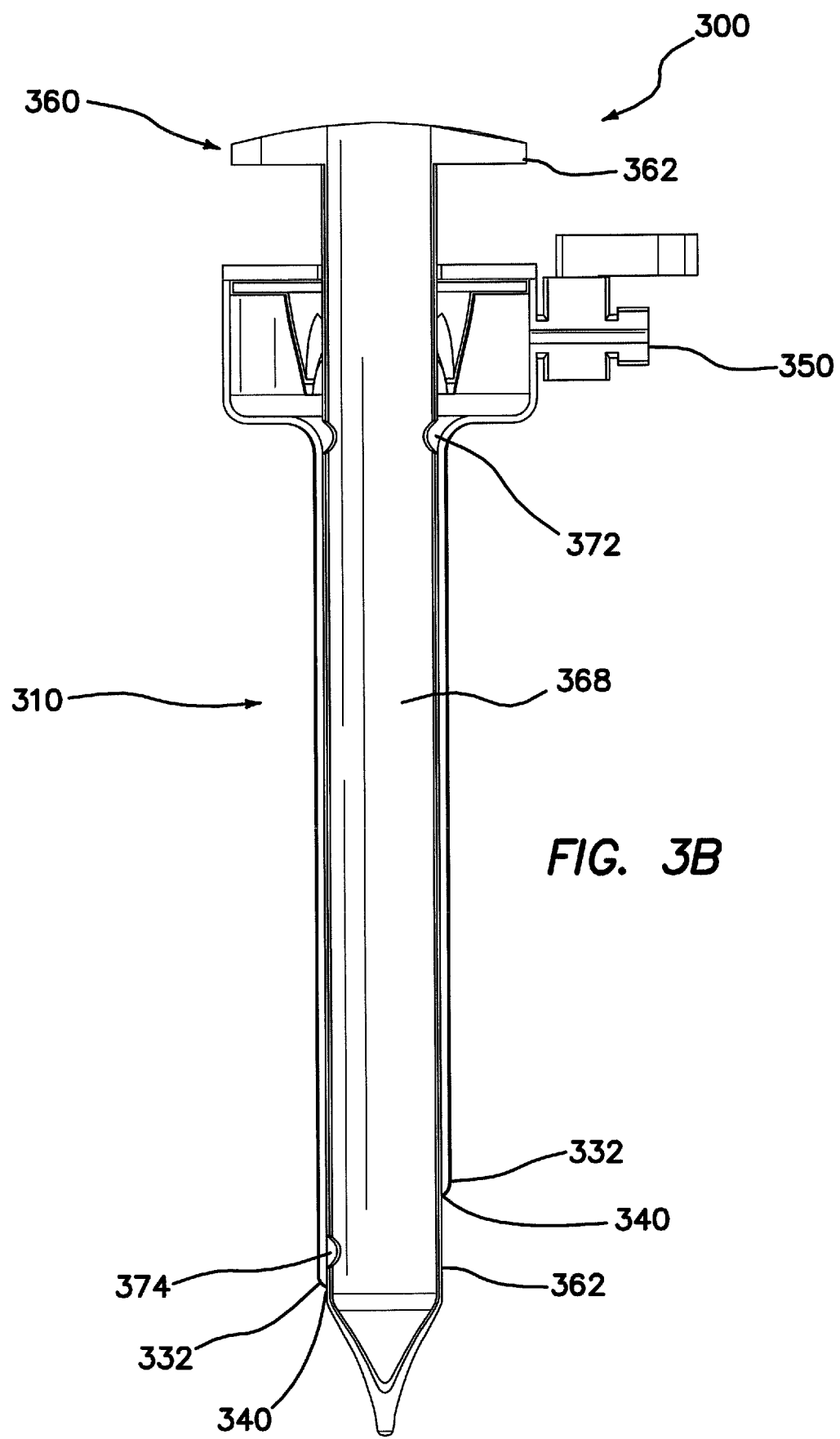
FIG. 3B is a side cross section of the insufflating access system illustrated in FIG. 3A in a closed configuration.

FIG. 3A is a perspective view of another embodiment of an insufflating access system 300 in an open configuration. FIG. 3B is a side cross section of the insufflating access system 300 illustrated in FIG. 3A in a closed configuration. The embodiment of the access system 300 illustrated in FIGS. 3A and 3B is similar to the embodiments described above. Like the embodiment illustrated in FIGS. 2A-2D, a gas flow channel in the illustrated embodiment incorporates an instrument well, thereby increasing the cross sectional area thereof. The access system 300 comprises a trocar 310 and an obturator 360.

As best seen in FIG. 3B, the obturator 360 comprises at least one proximal opening 372 and at least one distal opening 374, both of which perforate the body 362 of the obturator into the instrument well 368. In the illustrated embodiment, the at least one proximal opening 372 and the at least one distal opening 374 are both generally circular or oval, but in other embodiments, independently have other suitable shapes.

A fluid flow seal 340 is disposed at or integrated with the cannula tip 332 in the illustrated embodiment, as described above. Some embodiments of the trocar 310 further comprise a second fluid flow seal, either in addition to or instead of the fluid flow seal 340. Some embodiments of the second fluid flow seal comprise a tubular member, disposed in the seal assembly 320, through which the obturator extends, wherein the tubular member comprises at least one opening that is aligned with the at least one proximal opening 372 when the obturator is in an open position, thereby permitting fluid flow therethrough. The at least one opening in the tubular member is not aligned with the at least one proximal opening 372 when the obturator is in a closed position, thereby preventing fluid flow therethrough.

In the illustrated embodiment, the access system 300 is converted from the open configuration illustrated in FIG. 3A to the closed configuration illustrated in FIG. 3B by rotating the obturator 360, for example, using the handle 362. In the illustrated embodiment, the obturator 360 is rotated about 180° between the views illustrated in FIGS. 3A and 3B, although those skilled in the art will understand that other rotational angles are used in other embodiments. The particular rotational angle depends on factors including the size and shape of the distal opening 374, the location of the distal opening 374, the location of the fluid flow seal 340, the angle of the fluid flow seal 340. In the illustrated embodiment, fluid flows from the fluid port 350, into the proximal opening 372, into the instrument well 368, and out of the distal opening 374. In the illustrated embodiment, the distal opening 374 is exposed in the open configuration. In the closed configuration, the distal opening 374 is positioned proximal of the fluid flow seal 340, which forms a seal with a portion of the body 362 of the obturator distal of the distal opening 374, thereby preventing fluid flow therefrom.

Figure 3C:
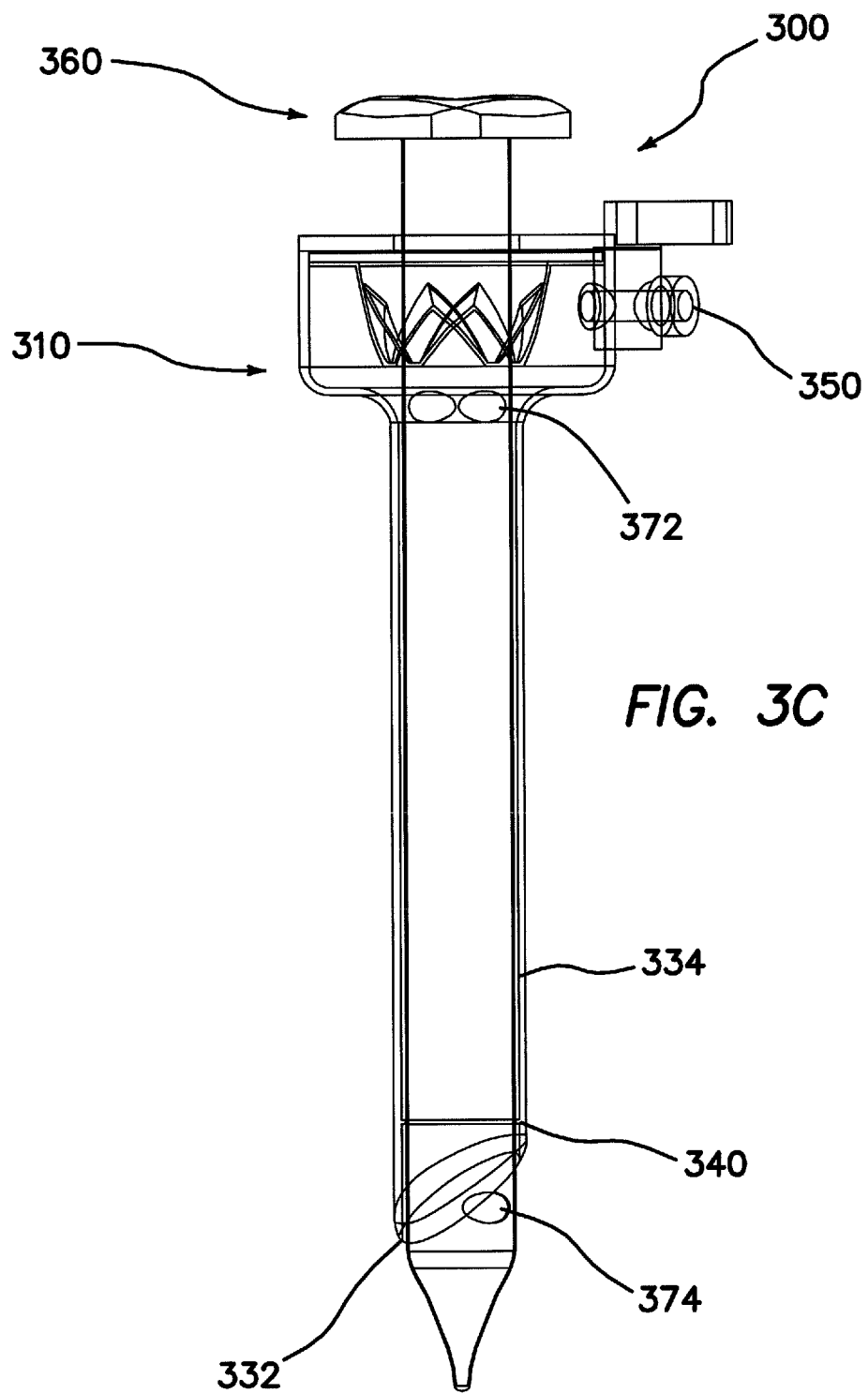
FIG. 3C is a side see-through view of another embodiment of an insufflating access system in an open configuration.

FIG. 3C is a see-through view of another embodiment of an insufflating access system 300 in an open configuration. In the illustrated embodiment, the trocar 310 is similar to the embodiment illustrated in FIGS. 1A-1F in which the fluid flow seal 340 is disposed in the lumen 334 of the cannula proximal to the tip 332. In the illustrated embodiment, the access system 300 is converted from the illustrated open configuration to a closed configuration by withdrawing the obturator longitudinally toward the proximal end, thereby positioning the distal opening 374 proximal of the fluid flow seal 340. The fluid flow seal 340 seals with a portion of the body 362 of the obturator distal of the distal opening 374, thereby preventing fluid flow therefrom.

Figure 4A:
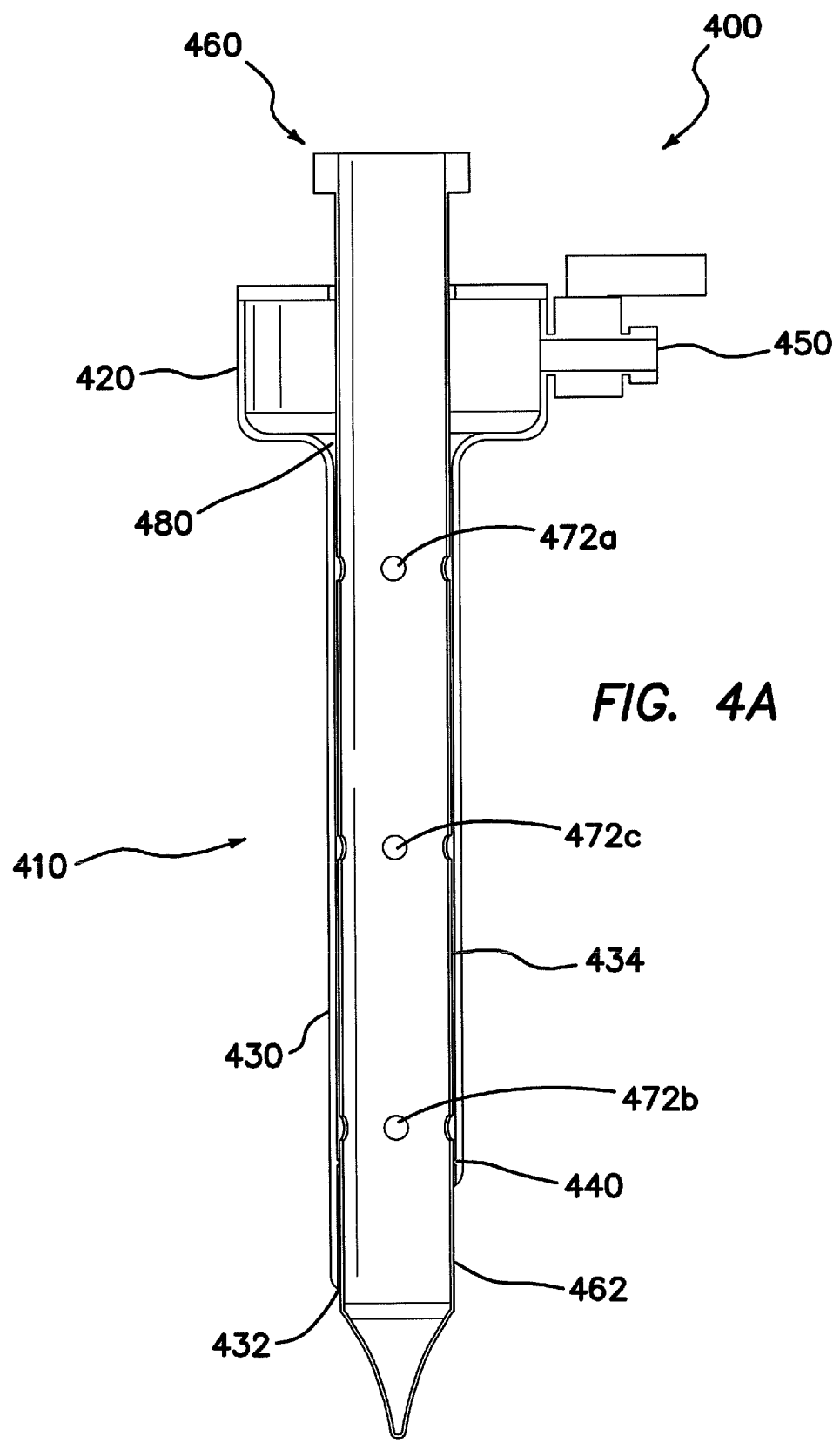
FIG. 4A is a side cross section of another embodiment of an insufflating access system in a closed configuration.
Figure 4B:
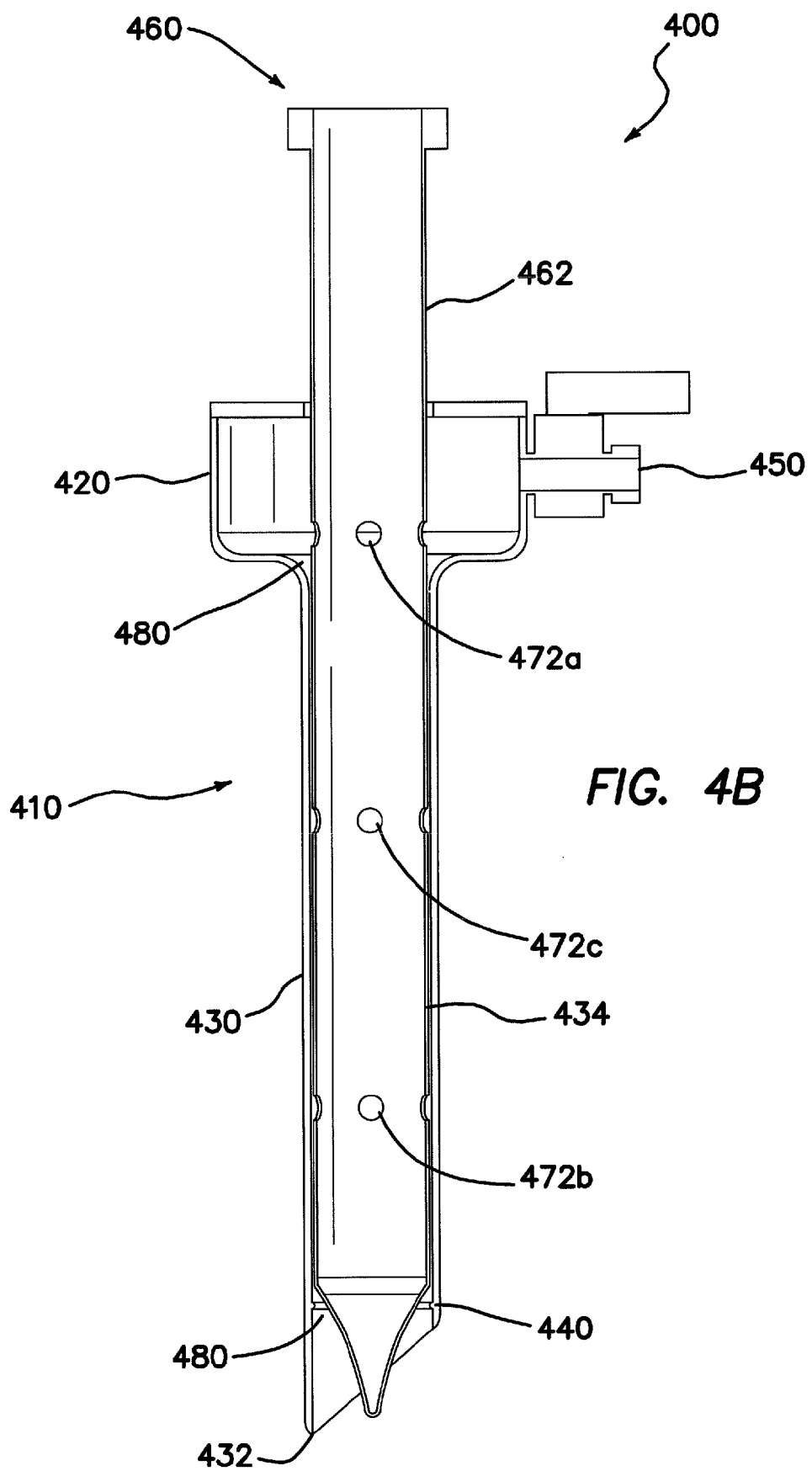
FIG. 4B is a side cross section of the insufflating access system illustrated in FIG. 4A in an open configuration.

FIG. 4A is a side cross section of another embodiment of an insufflating access system 400 in a closed configuration. FIG. 4B is a side cross section of the insufflating access system 400 illustrated in FIG. 4A in an open configuration. The insufflating access system 400 is generally similar to the insufflating access systems described above, and comprises a trocar 410 and an obturator 460. In the illustrated embodiment, the trocar 410 is generally similar to the embodiment illustrated in FIGS. 1A-1F and described above. The trocar 410 comprises a fluid flow seal 440 disposed in the lumen 434 of a cannula 430 thereof, proximal of the tip 432 of the cannula. In the illustrated embodiment, the fluid flow seal 440 is generally perpendicular to a longitudinal axis of the trocar 310.

Figure 4C:
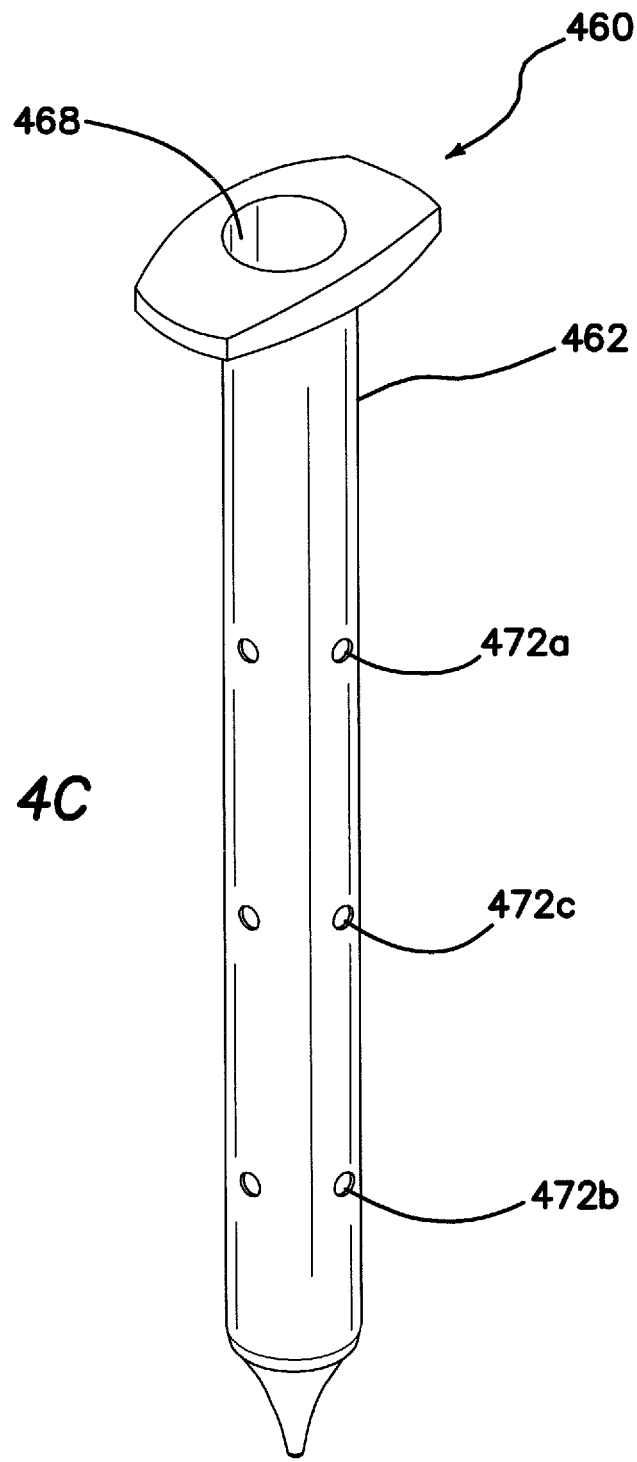
FIG. 4C is a perspective view of an embodiment of an obturator of the insufflating access system illustrated in FIGS. 4A and 4B.

As best seen in FIG. 4C, which is a perspective view of an embodiment of an obturator 460, the obturator 460 comprises a plurality of openings 472 disposed longitudinally and circumferentially on the body 462 of the obturator, which extend into the instrument well 468. The illustrated embodiment comprises a plurality of proximal openings 472a, a plurality of distal openings 472b, and a plurality of optional intermediate openings 472c.

In converting the access system 400 from the closed configuration illustrated in FIG. 1A to the open configuration illustrated in FIG. 4B, the obturator 460 is translated proximally along the longitudinal axis. In the closed configuration illustrated in FIG. 4A, the fluid flow seal 440 seals with a portion of the body 462 of the obturator distal of the distal openings 472b, thereby preventing fluid flow out of the tip 432 of the cannula at the distal end of access system 400. In the open configuration illustrated in FIG. 4B, because the body 462 of the obturator is proximal of the fluid flow seal 440, the body 462 and fluid flow seal 440 do not cooperate in forming a seal in the fluid flow channel 480. Accordingly, fluid flow is possible from the fluid port 450 into and through the fluid flow channel 480. In the illustrated embodiment, the fluid flow channel 480 comprises both the instrument well 468 and a space between the lumen 434 of the cannula and the body 462 of the obturator. As best seen in FIG. 4B, in the illustrated embodiment, the proximal openings 472a are disposed proximal to the cannula 430 within the trocar seal assembly 420, thereby increasing a cross sectional area around the proximal openings 472a and increasing fluid flow therethrough. Fluid continues flowing longitudinally towards the distal end of the access system 400 through both the instrument well 468 and the space between the lumen 434 of the cannula and the body 462 of the obturator. At the distal end of the obturator 460, fluid exits the instrument well 468 through the distal openings 472c and continues distally in the space between the lumen 434 of the cannula and the body 462 of the obturator. The fluid exits the access system 400 through the tip 432.

Although embodiments of the insufflating access system are applicable to any endoscopic application using insufflation, a prototypical application is in laparoscopic procedures. Consequently, for purposes of illustration only, the following describes an embodiment of a method for inserting an endoscopic port or trocar of an insufflating access system, and establishing pneumoperitoneum in laparoscopic surgery with reference to the embodiment illustrated in FIGS. 1A-1F.

Those skilled in the art will understand that the method is also applicable to other embodiments of the access system disclosed herein.

The obturator 160 is inserted into the trocar 110 and positioned in the closed configuration illustrated in FIG. 1E. A laparoscope is inserted into the instrument well 168 of the obturator and the laparoscope coupled with an imaging system, for example, a camera and a video monitor. The fluid port 150 is fluidly coupled to a source of pressurized insufflation gas.

Figure 5A:
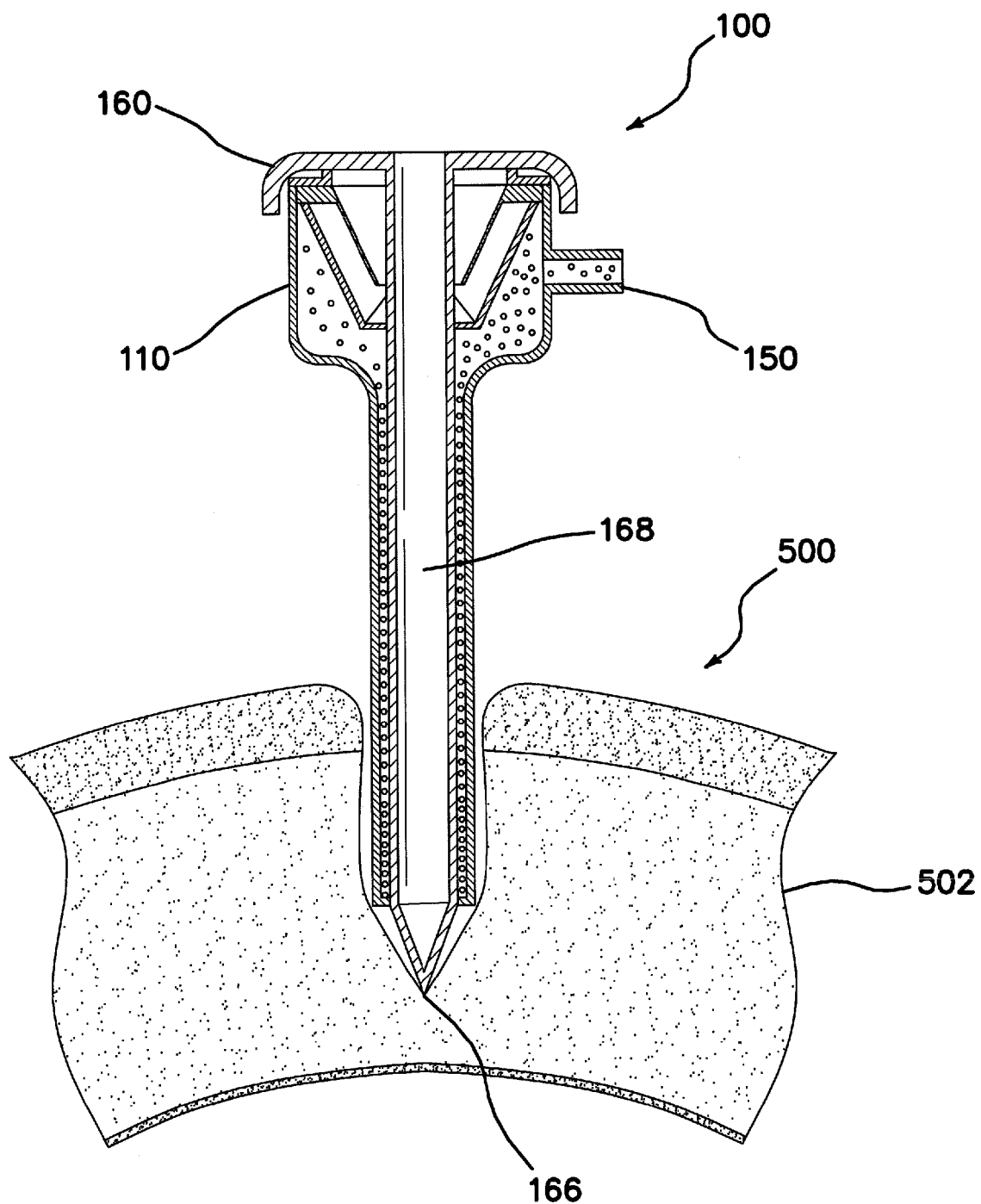
FIG. 5A-5C schematically illustrate an embodiment of a method for placing the embodiment of the access device illustrated in FIGS. 1A-1F.
Figure 5B:
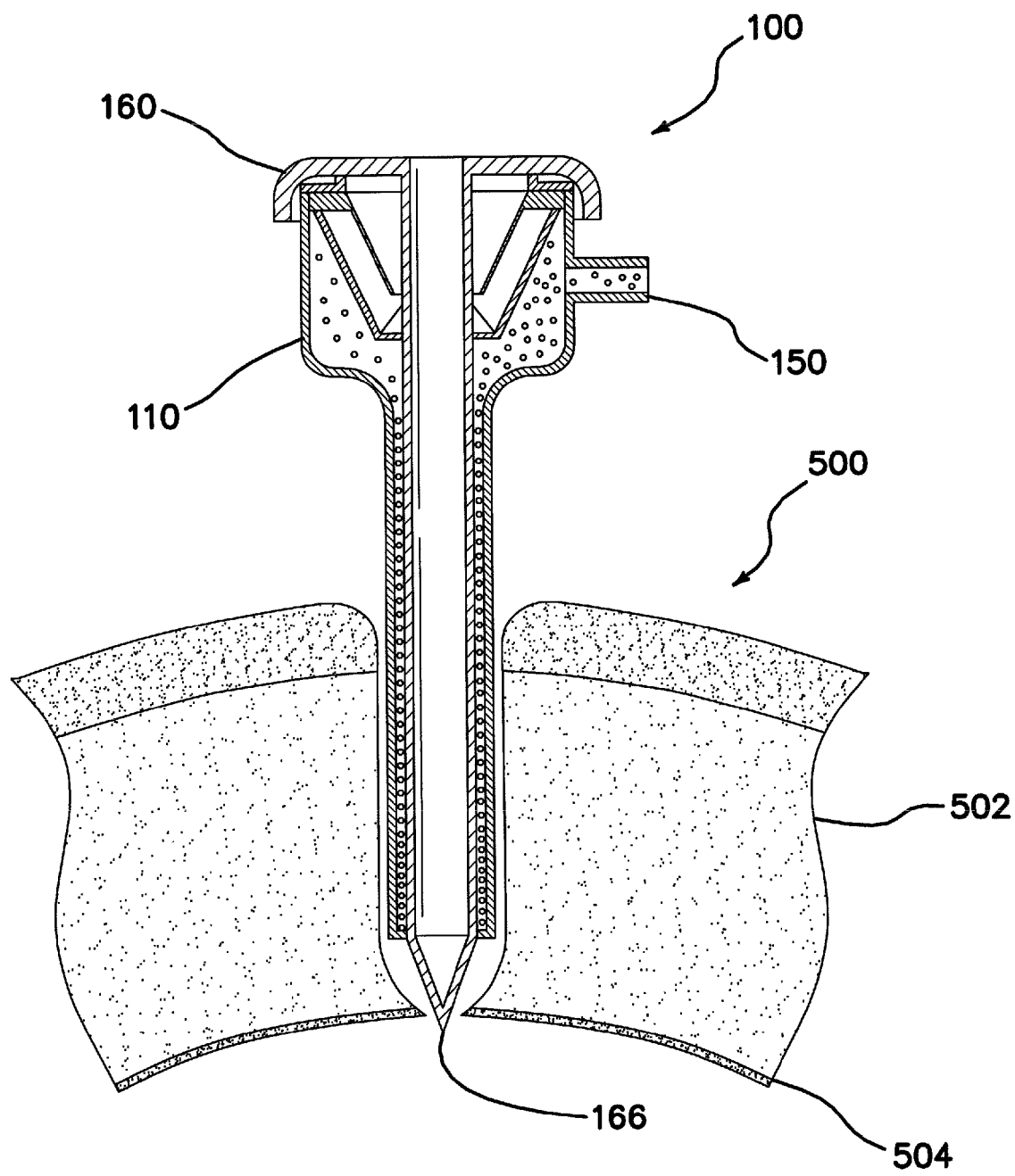
Figure 5C:
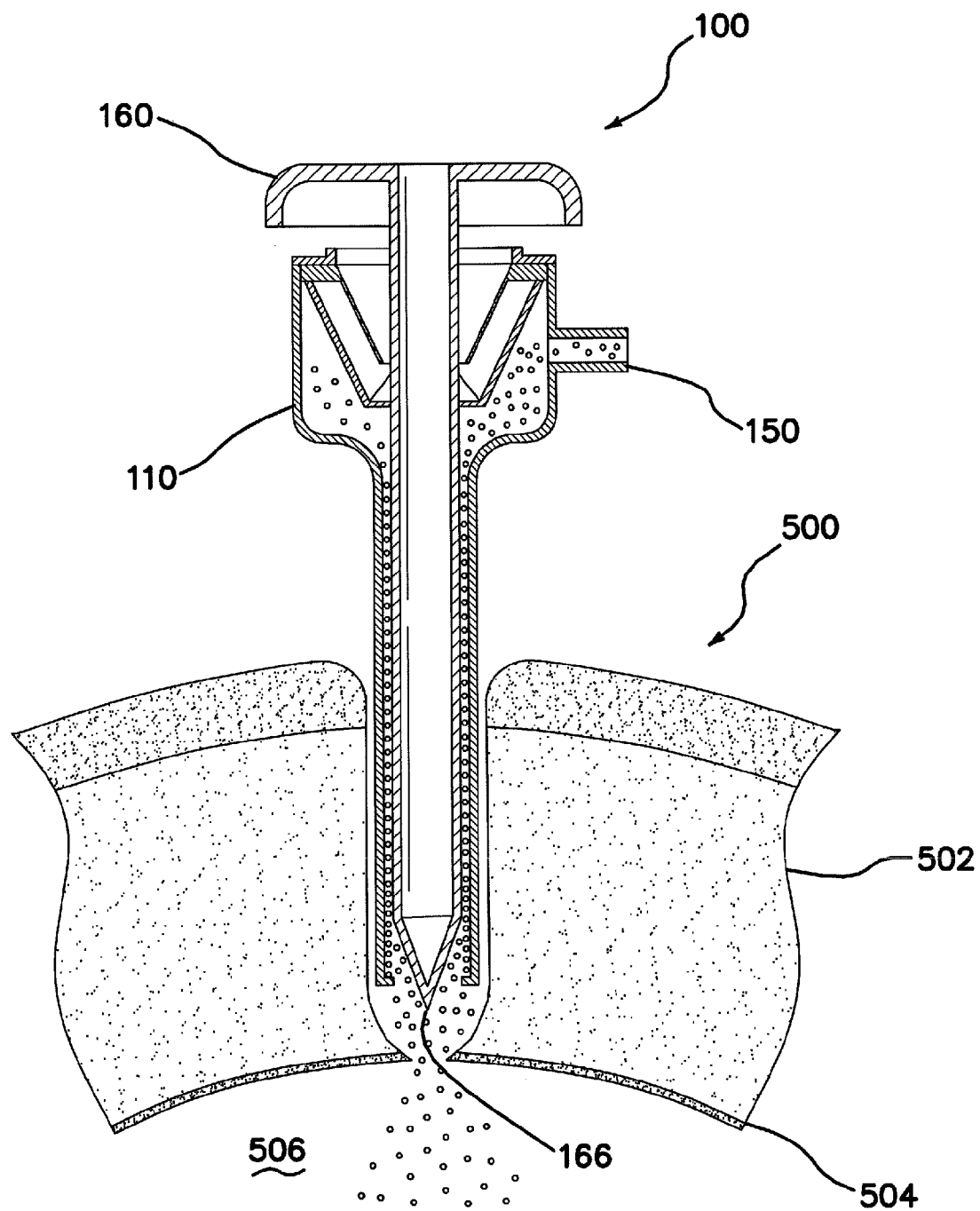

The user positions the tissue penetrating tip 166 in an incision made at a desired location on the patient's abdomen 500 and advances the insufflating access system 100 through the abdominal wall 502 as illustrated schematically in FIG. 5A. The user monitors the position of the tip 166 through the laparoscope and imaging system. When the user observes the tip 166 penetrating the peritoneum 504, as illustrated in FIG. 5B, the user converts the access system 100 to the open configuration. In the illustrated embodiment, the user urges the obturator 160 proximally, for example, pulling on the handle 162 to convert the access system 100 to the open configuration illustrated in FIG. 1F. As discussed above, in some embodiments, the obturator 160 and/or trocar 110 comprise one or more marks or indicia that indicate the position of the obturator 160 in the open position. With the access system 100 in the open configuration, insufflation gas flows from the source of insufflation gas, into the fluid port 150, into the proximal end 182 of the fluid flow channel, longitudinally through the fluid flow channel 180, past the fluid flow seal 140, past the partially withdrawn tip 166 of the obturator, and out the tip 132 of the cannula. Some gas may also flow out of the vents 136, particularly if the tip 132 of the cannula is fully or partially blocked. The gas flows through the opening in the peritoneum into the abdominal cavity, thereby insufflating the abdominal cavity 506 and establishing pneumoperitoneum as illustrated in FIG. 5C.

Accordingly, embodiments of the access system 100 and method provide an accurate and simple method for gaining access to the abdominal cavity for laparoscopic surgery. In other embodiments, the insufflating access system 100 provides access to the abdominal cavity through another surface adjacent to the peritoneal lining of the abdominal cavity, for example, the cul-de-sac of the vagina, any point along the gastrointestinal tract from the diaphragm to the anus, or one of the great vessels such as the abdominal aorta or vena cava. Embodiments of the access system 100 and method provide access to other internal structures, for example, the kidney, the stomach, and/or the third ventricle of the brain, or any hollow organ for which accurate and shallow entry and the subsequent flow of gas or liquid is desired.

Disposing a fluid flow seal 140 between the obturator 160 and the distal end 114 of the cannula permits the device 100 to be fluidly coupled with a source of $CO_2$ while the device 100 is advanced through the abdominal wall 502. As soon as the peritoneum 504 is punctured by the tip 166 of the obturator, the surgeon stops forward movement of the device 100 and dislocates the fluid flow seal 140 between the obturator 160 and the cannula 130, thereby allowing the gas to flow through the gas flow channel 180 and out of the device 100. The gas, following a path of least resistance, flows between the tip 166 and the abdominal wall 502, through the opening made in the peritoneum 504, and finally into the abdominal cavity 504. Consequently, pneumoperitoneum is established with reduced penetration into the organ bed because the tip 166 of the obturator does not extend as far beyond the peritoneum as in embodiments in which the tip comprises vent holes through which gas insufflates the abdominal cavity. Embodiments of the device 100 also do not comprise at least one of: seals within the obturator and gas channels around the laparoscope. Some embodiments eliminate or reduce the possibility of fluid and/or tissue entering the visual field within the obturator tip 166. In some embodiments, the peritoneum 504 is punctured and the abdominal cavity 504 insufflated without further penetration of the tip 166 beyond the peritoneum 504 and into the abdominal cavity 506 or organ bed.

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. An insufflating surgical access system comprising:
   a trocar comprising:
      a proximal end and a distal end;
      a trocar seal assembly disposed at the proximal end of the trocar, the trocar seal assembly comprising an instrument seal;
      an elongate cannula disposed at the distal end of the trocar, the cannula comprising a tubular wall defining a lumen, an open proximal end, and an open distal end;
      an access channel defining a longitudinal axis, extending through the trocar seal assembly and the lumen of the cannula, from the proximal end of the trocar to the distal end of the trocar;
      a fluid port disposed at the proximal end of the trocar; and
      a fluid flow seal disposed in the access channel;
   an obturator comprising:
      an elongate body comprising a proximal end and a distal end;
      a tissue penetrating tip disposed at the distal end; and
      a handle disposed at the proximal end,
      wherein the obturator is slidably insertable into the proximal end of the access channel, and the tip of the obturator extends out of the distal, open end of the cannula when fully inserted therethrough; and
   a fluid flow channel fluidly connected to the fluid port of the trocar, and extending to a distal end of the insufflating access system,
   wherein the fluid flow channel comprises at least one proximal opening disposed in the elongate body of the obturator and at least one distal opening disposed in the elongate body of the obturator;
   wherein the obturator in the access channel has
      a closed position, in which the body of the obturator sealingly contacts the fluid flow seal, thereby preventing gas flow through the fluid flow channel, and
      an open position, in which the distal opening is exposed, thereby allowing fluid flow through the fluid flow channel;
   and
   wherein the access system is converted from the closed position to the open position by rotating the obturator in the access channel to uncover the at least one distal opening to allow gas flow through the at least one distal opening.

2. The access system of claim 1, wherein trocar seal assembly further comprises a zero seal.

3. The access system of claim 1, wherein the tissue penetrating tip does not comprise vent holes.

4. The access system of claim 1, wherein the distal end of the cannula comprises an angled tip.

5. The access system of claim 1, wherein the fluid port is disposed on the trocar seal assembly.

6. The access system of claim 1, wherein the fluid flow seal is integrated with a cannula tip disposed at the distal end of the cannula.

7. The access system of claim 1, wherein the fluid flow seal is disposed proximal of the distal end of the cannula.

8. The access system of claim 1 wherein the fluid flow seal is substantially perpendicular to the longitudinal axis of the axis channel.

9. The access system of claim 1, wherein the fluid flow seal is not perpendicular to the longitudinal axis of the axis channel.

10. The access system of claim 1, wherein the obturator further comprises an instrument well open at a proximal end of the obturator, extending longitudinally through the body of the obturator, terminating at the tip of the obturator, and dimensioned to receive a laparoscope therein, wherein at least a portion of the tip of the obturator is transparent.

11. The access system of claim 10, further comprising a laparoscope.

12. The access system of claim 1, wherein the fluid flow channel comprises a space defined by the lumen of the cannula and the body of the obturator.

13. The access system of claim 1, wherein the fluid flow channel comprises an instrument well disposed in the body of the obturator.

14. A method for insufflating a body cavity using the insufflating surgical access system of claim 1, the method comprising:
positioning the obturator in the closed position;
fluidly connecting the fluid port with a source of insufflation gas;
positioning the tissue penetrating tip at a desired position;
advancing the tissue penetrating tip through a body wall until the tip enters a body cavity; and
positioning the obturator in the open position, fluidly connecting the fluid port with the body cavity through the fluid flow channel, thereby insufflating the body cavity.

15. The method of claim 14, further comprising visually monitoring the position of the penetrating tip through a laparoscope.

16. An insufflating surgical access system comprising:
a trocar comprising:
a proximal end and a distal end;
a trocar seal assembly disposed at the proximal end of the trocar, the trocar seal assembly comprising an instrument seal;
an elongate cannula disposed at the distal end of the trocar, the cannula comprising a tubular wall defining a lumen, an open proximal end, and an open distal end;
an access channel defining a longitudinal axis, extending through the trocar seal assembly and the lumen of the cannula, from the proximal end of the trocar to the distal end of the trocar;
a fluid port disposed at the proximal end of the trocar; and
a fluid flow seal disposed in the access channel;
an obturator comprising:
an elongate body comprising a proximal end and a distal end;
a tissue penetrating tip disposed at the distal end; and
a handle disposed at the proximal end,
wherein the obturator is slidably insertable into the proximal end of the access channel, and the tip of the obturator extends out of the distal, open end of the cannula when fully inserted therethrough; and
a fluid flow channel fluidly connected to the fluid port of the trocar, and extending to a distal end of the insufflating access system,
wherein the fluid flow channel comprises a slot having a proximal end and a distal end disposed in the elongate body of the obturator; the slot extending longitudinally from the proximal end to the distal end of the elongate body of the obturator;
wherein the obturator in the access channel has
a closed position, in which the distal end of the slot is positioned such that fluid does not flow from the slot thereby preventing fluid flow through the fluid flow channel, and
an open position that permits fluid flow from the distal end of the slot, thereby allowing fluid flow through the fluid flow channel.

17. The access system of claim 16, wherein in the closed position, the obturator is displaced distally in the access channel compared with the open position.

18. The access system of claim 16, wherein in the closed position, the obturator is displaced proximally in the access channel compared with the open position.

19. The access system of claim 16, wherein in the closed position, the obturator is rotated in the access channel compared with the open position.

20. The access system of claim 16, wherein the proximal end of the slot is disposed below the instrument seal of the trocar seal assembly in fluid communication with the fluid port.

* * * * *